US012774312B2

(12) United States Patent
Hughes et al.

(10) Patent No.: US 12,774,312 B2
(45) Date of Patent: Oct. 27, 2026

(54) COMPOSITIONS AND METHODS FOR COMBATING MULTIDRUG-RESISTANT BACTERIA

(71) Applicant: University of Virginia Patent Foundation, Charlottesville, VA (US)

(72) Inventors: Molly A. Hughes, Charlottesville, VA (US); Matthew Crawford, Charlottesville, VA (US); Rachel Letteri, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 1152 days.

(21) Appl. No.: 17/262,667

(22) PCT Filed: Jul. 24, 2019

(86) PCT No.: PCT/US2019/043298

§ 371 (c)(1),
(2) Date: Jan. 22, 2021

(87) PCT Pub. No.: WO2020/023670

PCT Pub. Date: Jan. 30, 2020

(65) Prior Publication Data

US 2021/0300981 A1 Sep. 30, 2021

Related U.S. Application Data

(60) Provisional application No. 62/743,662, filed on Oct. 10, 2018, provisional application No. 62/702,557, filed on Jul. 24, 2018.

(51) Int. Cl.

*C07K 14/52* (2006.01)
*A61P 31/04* (2006.01)
*A61K 38/00* (2006.01)

(52) U.S. Cl.

CPC ............ *C07K 14/522* (2013.01); *A61P 31/04* (2018.01); *A61K 38/00* (2013.01)

(58) Field of Classification Search

CPC ............................... C07K 14/522; A61P 31/04
See application file for complete search history.

(56) References Cited

U.S. PATENT DOCUMENTS

| | | | |
|---|---|---|---|
| 2007/0066523 | A1 | 3/2007 | Merzouk et al. |
| 2007/0160574 | A1 | 7/2007 | Merzouk et al. |
| 2013/0195800 | A1 | 8/2013 | Roeth et al. |
| 2016/0068959 | A1 | 3/2016 | Lau et al. |

FOREIGN PATENT DOCUMENTS

| | | | |
|---|---|---|---|
| WO | WO 2013/032964 | A1 | 3/2013 |
| WO | WO 2016/176147 | A1 | 11/2016 |

OTHER PUBLICATIONS

Li H, Anuwongcharoen N, Malik AA, Prachayasittikul V, Wikberg JE, Nantasenamat C. Roles of d-Amino Acids on the Bioactivity of Host Defense Peptides. Int J Mol Sci. Jun. 30, 2016;17(7):1023. (Year: 2016).*

International Search Report corresponding to PCT/2019/043298 dated Dec. 4, 2019.

Jamieson et al. (2010) Influenza Virus-Induced Glucocorticoids Compromise Innate Host Defense Against a Secondary Bacterial Infection. Cell Host Microbe 7(2):103-114.

Written Opinion corresponding to PCT/2019/043298 dated Dec. 4, 2019.

Cole AM, Ganz T, Liese AM, Burdick MD, Liu L, Strieter RM. Cutting edge: IFN-inducible ELR- CXC chemokines display defensin-like antimicrobial activity. J Immunol. 2001. 167(2):623-627. PMID: 11441062.

Hieshima K, Ohtani H, Shibano M, Izawa D, Nakayama T, Kawasaki Y, Shiba F, Shiota M, Katou F, Saito T, Yoshie O. CCL28 has dual roles in mucosal immunity as a chemokine with broad-spectrum antimicrobial activity. J Immunol. 2003. 170(3): 1452-1461. PMID: 12538707.

(Continued)

*Primary Examiner* — Aurora M Fontainhas
*Assistant Examiner* — Jennifer A Benavides
(74) *Attorney, Agent, or Firm* — Thomas | Horstemeyer LLP

(57) ABSTRACT

Provided are peptides, modified peptides, fragments thereof, conjugates thereof, and polymers thereof that have antibacterial activity against bacterial that include but are not limited to multidrug-resistant bacteria. In some embodiments, the presently disclosed subject matter relates to peptides that include the amino acid sequences RTVRCTCI (SEQ ID NO: 2), LSRTVRCTCISI (SEQ ID NO: 3) or VPLSRTVRCTCISI (SEQ ID NO: 4), PESK AIKNLLK AV SKERSKRSP (SEQ ID NO: 11), or KNLLK AV SKERSKRSP (SEQ ID NO: 12), modified peptides thereof, fragments thereof, and conjugates thereof, and any combination thereof. The peptides, modified peptides, fragments thereof, and conjugates thereof can be polymer-functionalized, encapsulated in a particle, embedded in and/or on a solid support, optionally wherein the peptide is formulated for release from the solid support, impregnated in a dressing, optionally wherein the peptide is formulated for release from the dressing, and/or is formulated for use in a nebulizer, for topical administration, and/or for systemic administration. Also provided are medical devices having a support layer with an antibacterial agent embedded therein or associated therewith, methods for inhibiting the growth of and/or killing bacteria, for recruiting immune cells to site of infection, for treating or preventing community and/or nosocomial infections, for inducing a subject's immune system against a pathogen, for treating bacterial infections present in wounds, for treating pulmonary infections, for treating or preventing systemic bacterial infections, and for combination therapies with conventional antibiotics.

13 Claims, 14 Drawing Sheets

Specification includes a Sequence Listing.

(56) References Cited

OTHER PUBLICATIONS

Yang D, Chen Q, Hoover DM, Staley P, Tucker KD, Lubkowski J, Oppenheim JJ. Many chemokines including CCL20/MIP-3alpha display antimicrobial activity. J Leukoc Biol. 2003. 74(3):448-455. PMID: 12949249.
Yeaman MR, Yount NY, Waring AJ, Gank KD, Kupferwasser D, Wiese R, Bayer AS, Welch WH. Modular determinants of antimicrobial activity in platelet factor-4 family kinocidins. Biochim Biophys Acta. 2007. 1768(3): 609-619. PMID: 17217910.
Björstad A, Fu H, Karlsson A, Dahlgren C, Bylund J. Interleukin-8-derived peptide has antibacterial activity. Antimicrob Agents Chemother. 2005. 49(9):3889-3895. PMID: 16127067.
Yount NY, Waring AJ, Gank KD, Welch WH, Kupferwasser D, Yeaman MR. Structural correlates of antimicrobial efficacy in IL-8 and related human kinocidins. Biochim Biophys Acta. 2007. 1768(3): 598-608. PMID: 17208195.
Martínez-Becerra F, Silva DA, Domínguez-Ramírez L, Mendoza-Hernández G, López-Vidal Y, Soldevila G, García-Zepeda EA. Analysis of the antimicrobial activities of a chemokine-derived peptide (CDAP-4) on Pseudomonas aeruginosa. Biochem Biophys Res Commun. 2007. 355(2):352-358. PMID: 17307153.
Chan DI, Hunter HN, Tack BF, Vogel HJ. Human macrophage inflammatory protein 3alpha: protein and peptide nuclear magnetic resonance solution structures, dimerization, dynamics, and anti-infective properties. Antimicrob Agents Chemother. 2008. 52(3): 883-894. PMID: 18086840.
Booth V, Keizer DW, Kamphuis MB, Clark-Lewis I, Sykes BD. The CXCR3 binding chemokine IP-10/CXCL10: structure and receptor interactions. Biochemistry. 2002. 41(33):10418-10425. PMID: 12173928.
Clark-Lewis I, Mattioli I, Gong JH, Loetscher P. Structure-function relationship between the human chemokine receptor CXCR3 and its ligands. J Biol Chem. 2003. 278(1):289-295. PMID: 12417585.
Campanella GSV, Lee EMJ, Sun J, Luster Ad. CXCR3 and heparin binding sites of the chemokine IP-10 (CXCL10). J Biol Chem. 2003. 278(19):17066-17074. PMID: 12571234.
Binder U, Skerra A. Strategies for extending the half-life of biotherapeutics: successes and complications. Expert Opin Biol Ther. 2025. 25(1): 93-118. PMID: 39663567.
Wang L, Wang N, Zhang W, Cheng X, Yan Z, Shao G, Wang X, Wang R, Fu C. Therapeutic peptides: current applications and future directions. Signal Transduct Target Ther. 2022. 7(1):48. PMID: 35165272.
Garton M, Nim S, Stone TA, Wang KE, Deber CM, Kim PM. Method to generate highly stable D-amino acid analogs of bioactive helical peptides using a mirror image of the entire PDB. Proc Natl Acad Sci U S A. 2018. 115(7):1505-1510. PMID: 29378946.
Zhao Y, Zhang M, Qiu S, Wang J, Peng J, Zhao P, Zhu R, Wang H, Li Y, Wang K, Yan W, Wang R. Antimicrobial activity and stability of the D-amino acid substituted derivatives of antimicrobial peptide polybia-MPI. AMB Express. 2016. (1):122. PMID: 27900727.
Feng Z, Xu B. Inspiration from the mirror: D-amino acid containing peptides in biomedical approaches. Biomol Concepts. 2016. 7(3):179-187. PMID: 27159920.
Li C, Zhan C, Zhao L, Chen X, Lu WY, Lu W. Functional consequences of retro-inverso isomerization of a miniature protein inhibitor of the p53-MDM2 interaction. Bioorg Med Chem. 2013. 21(14):4045-4050.
Najjar K, Erazo-Oliveras A, Brock DJ, Wang TY, Pellois JP. An L- to D-amino acid conversion in an endosomolytic analog of the cell-penetrating peptide TAT influences proteolytic stability, endocytic uptake, and endosomal escape. J Biol Chem. 2017. 292(3): 847-861. PMID: 27923812.
Jia F, Wang J, Peng J, Zhao P, Kong Z, Wang K, Yan W, Wang R. D-amino acid substitution enhances the stability of antimicrobial peptide polybia-CP. Acta Biochim Biophys Sin. 2017. 49(10): 916-925. PMID: 28981608.
Díaz-Perlas C, Varese M, Guardiola S, Sánchez-Navarro M, García J, Teixido M, Giralt E. Protein chemical synthesis combined with mirror-image phage display yields D-peptide EGF ligands that block the EGF-EGFR interaction. Chembiochem. 2019. 20(16):2079-2084. PMID: 31268623.
Wtły J, Szarszoń K, Sabieraj M, Kola A, Wieczorek R, Janek T, Valensin D. Modulating copper(II) coordination and antimicrobial activity: effects of D-amino acid substitution and retro-inverso modification in human saliva MUC7 peptide. Inorg Chem. 2025. 64(12):6365-6377. PMID: 40105798.
Tugyi R, Uray K, Iván D, Fellinger E, Perkins A, Hudecz F. Partial D-amino acid substitution: improved enzymatic stability and preserved Ab recognition of a MUC2 epitope peptide. Proc Natl Acad Sci U S A. 2005. 102(2):413-418. PMID: 15630090.
Rabideau AE, Pentelute BL. A D-amino acid at the N-terminus of a protein abrogates its degradation by the N-end rule pathway. ACS Cent Sci. 2015. 1(8):423-430. PMID: 26807441.
Lohan S, Konshina AG, Mohammed EHM, Helmy NM, Jha SK, Tiwari RK, Maslennikov I, Efremov RG, Parang K. Impact of stereochemical replacement on activity and selectivity of membrane-active antibacterial and antifungal cyclic peptides. NPJ Antimicrob Resist. 2025. 3(1):56. PMID: 40527928.
D'Aloisio V, Dognini P, Hutcheon GA, Coxon CR. PepTherDia: database and structural composition analysis of approved peptide therapeutics and diagnostics. Drug Discov Today. 2021. 26(6):1409-1419. PMID: 33647438.
M.A. Crawford, D.E. Lowe, D.J. Fisher, S. Stibitz, R.D. Plaut, J.W. Beaber, J. Zemansky, B. Mehrad, I.J. Glomski, R.M. Strieter, & M.A. Hughes, Identification of the bacterial protein FtsX as a unique target of chemokine-mediated antimicrobial activity against Bacillus anthracis, Proc. Natl. Acad. Sci. U.S.A. 108 (41) 17159-17164, https://doi.org/10.1073/pnas. 1108495108 (2011).
Margulieux KR, Fox JW, Nakamoto RK, Hughes Ma. CXCL10 Acts as a Bifunctional Antimicrobial Molecule against Bacillus anthracis. mBio. May 10, 2016;7(3):e00334-16. doi: 10.1128/mBio. 00334-16. PMID: 27165799; PMCID: PMC4959661.
Crawford MA, Margulieux KR, Singh A, Nakamoto RK, Hughes MA. Mechanistic insights and therapeutic opportunities of antimicrobial chemokines. Semin Cell Dev Biol. Apr. 2019; 88:119-128. doi: 10.1016/j.semcdb.2018.02.003. Epub Feb. 21, 2018. PMID: 29432954; PMCID: PMC6613794.
Crawford MA, Ward AE, Gray V, Bailer P, Fisher DJ, Kubicka E, Cui Z, Luo Q, Gray MC, CrissLetteri RA, Hughes MA. Disparate Regions of the Human Chemokine CXCL10 Exhibit Broad-Spectrum Antimicrobial Activity against Biodefense and Antibiotic-Resistant Bacterial Pathogens. ACS Infect Dis. Jan. 13, 2023;9(1):122-139. doi: 10.1021/acsinfecdis.2c00456. Epub Dec. 7, 2022. PMID: 36475632; PMCID: PMC9841529.

* cited by examiner

COMPOSITIONS AND METHODS FOR COMBATING MULTIDRUG-RESISTANT BACTERIA

CROSS REFERENCE TO RELATED APPLICATIONS

This application claims benefit of U.S. Provisional Application Ser. No. 62/702,557, filed Jul. 24, 2018, and U.S. Provisional Application Ser. No. 62/743,662, filed Oct. 10, 2018. The disclosure of each of these Provisional Applications is incorporated herein by reference in its entirety.

GRANT STATEMENT

This invention was made with government support under Grant Nos. R01 AI099097, F32 AI108249, and R21 AI139947 awarded by National Institutes of Health. The Government has certain rights in the invention.

TECHNICAL FIELD

The presently disclosed subject matter relates to compositions and methods useful for treating and preventing bacterial infections, which in some embodiments are caused by multidrug-resistant bacteria. In particular, the presently disclosed subject matter relates to peptide-based compositions with bactericidal activity that can be administered to subject to treat and/or prevent bacterial infections.

BACKGROUND

Since 1996, there has been a dramatic and alarming increase in the isolation of multidrug resistant (MDR) bacteria, such as *Klebsiella pneumoniae* and *Escherichia coli*, from patients with bloodstream infections, pneumonias, and intra-abdominal infections. Multi-drug resistance typically denotes bacteria resistant to three or more classes of antibiotics. The increase in MDR bacteria has now been recognized throughout the world and in a number of states within the United States. These MDR bacteria are resistant to not only the cephalosporins but also to the carbapenems (imipenem, meropenem, ertapenem, and doripenem), which have traditionally been the last line of antimicrobial defense against the cephalosporin-resistant organisms. So-called carbapenem-resistant Enterobacteriaceae (CRE) applies to Enterobacteriaceae such as *Klebsiella* spp., *Escherichia coli, Enterobacter* spp., *Citrobacter* spp., *Serratia* spp., *Salmonella* spp., *Shigella* spp., etc., which are characterized as being resistant to ≥3 classes of antibiotics, including carbapenems. Carbapenemases are enzymes that inactivate carbapenems, and include at least the following: *Klebsiella pneumoniae* carbapenemase (KPC), which is the most commonly encountered mechanism in United States; Oxacillinase (OXA-48), which is most commonly encountered in isolates from Europe and the Middle East; and New Delhi Metallo β-lactamase (NDM), which is most commonly encountered in Southern Asia, particularly in Pakistan and India, but also in the Balkans and Middle East. Of particular concern is that global distributions are spreading and evolving due to mobility and travel of humans. Genes for carbapenemases are located on chromosomes or, more commonly, plasmids, which are mobile, highly transmissible genetic elements found in many bacterial species. These organisms frequently carry multiple mechanisms of resistance in addition to carbapenemase, rendering them multidrug resistant.

Given that the carbapenems are not effective against CRE, there are now very few antimicrobial options available. In the absence of any new antibiotics to combat these pathogens, healthcare workers are being forced to use older antibiotics such as colistin, which was used in the 1970's and has significant and serious side effects. Moreover, colistin-resistant bacteria are now being identified, reducing the available armamentarium of antimicrobials to one or zero antibiotics.

Much of the focus in the last two decades has been on resistance in Gram-positive organisms (e.g., methicillin-resistant *Staphylococcus aureus* (MRSA) and vancomycin-resistant *Enterococcus* (VRE)), although Gram-negative bacteria account for a large proportion of nosocomial infections. For example, in New York City, Gram-negative organisms account for at least 8% of nosocomial infections, and at least half of those are MDR, carbapenem-resistant bacteria.

The list of antibiotics available to treat infections with any of these MDR CRE organisms is limited from very few to none. Approximately 60% of hospital patients in the United States received at least one dose of an antibacterial, of which perhaps about 50% might be inappropriate and could be at least partially responsible for the rise in antimicrobial resistance. Antimicrobial resistance accounts for about 8 million additional days of hospitalization and contributes to the majority of almost 100,000 annual hospital-acquired infection (HAI) related deaths. From 1998 to 2009, for example, the annual costs associated with infections caused by MDR bacterial pathogens rose from about $4 billion to about $21-34 billion. Concurrently, the total number of new antibacterial agents being developed has dropped from about 16 from 1983-1987 to just 1 between 2008 and 2012. Novel approaches are critically needed for identifying new therapies for treating such pathogens, especially since simply producing newer generation antibiotics of the same class is unlikely to provide much benefit since cross-resistance can rapidly develop.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The presently disclosed subject matter relates in some embodiments to peptides, peptide conjugates, and polymers thereof that have antibacterial activity. In some embodiments, a peptide of the presently disclosed subject matter comprises, consists essentially of, or consists of the amino acid sequence RTVRCTCI (SEQ ID NO: 2), or is a modified peptide thereof, a fragment thereof, a conjugate thereof, a polymer thereof, or any combination thereof. In some embodiments, the peptide, modified peptide thereof, fragment thereof, conjugate thereof, and/or polymer thereof has bactericidal and/or bacteriostatic activity against a bacterium selected from the group consisting of *Enterococcus faecium, Staphylococcus aureus, Klebsiella pneumoniae, Acinetobacter baumannii, Pseudomonas aeruginosa*, members of the family Enterobacteriaceae, including but not limited to *Escherichia coli, Klebsiella* spp., *Enterobacter cloacae*, and *Serratia* spp.; sexually-transmitted bacteria such as but not limited to *Neisseria gonorrhoeae*; enteric pathogens such as but not limited to a *Salmonella enterica* serovars such as but not limited to *Salmonella enterica* serovar *Typhi, Shigella flexneri*; and biothreat agents such as but not limited to *Bacillus anthracis* in both vegetative and spore forms. In some embodiments, the bacterium is an MDR strain of *Enterococcus faecium, Staphylococcus aureus, Klebsiella pneumoniae, Acinetobacter baumannii, Pseudomonas aeruginosa, Salmonella enterica*, optionally *Salmonella enterica* serovar *Typhi*, or *Shigella flexneri*.

In some embodiments, the peptide comprises, consists essentially of, or consists of the amino acid sequence LSRTVRCTCISI (SEQ ID NO: 3) or VPLSRTVRCTCISI (SEQ ID NO: 4), or is a modified peptide thereof, a fragment thereof, a conjugate thereof, and/or a polymer thereof.

The presently disclosed subject matter also relates in some embodiments to a peptide comprising, consisting essentially of, or consisting of the amino acid sequence PESKAIKNLLKAVSKERSKRSP (SEQ ID NO: 11) or KNLLKAVSKERSKRSP (SEQ ID NO: 12), a modified peptide thereof, a fragment thereof, a conjugate thereof, and/or a polymer thereof.

In some embodiments of the presently disclosed subject matter, one or more, optionally all, of the amino acids of the disclosed peptides, modified peptides, fragments thereof, conjugates thereof, and/or polymers thereof are D-amino acids.

In some embodiments, the peptide, modified peptide, fragment thereof, conjugate thereof, and/or polymer thereof is polymer-functionalized, encapsulated in a particle, embedded in and/or on a solid support, optionally wherein the peptide, modified peptide, fragment thereof, conjugate thereof, and/or polymer thereof is formulated for release from the solid support, impregnated in a dressing, optionally wherein the peptide, modified peptide, fragment thereof, conjugate thereof, and/or polymer thereof is formulated for release from the dressing, and/or is formulated for use in a nebulizer, for topical administration, and/or for systemic administration.

The presently disclosed subject matter also relates in some embodiments to conjugates and/or polymers comprising, consisting essentially of, or consisting of the peptides disclosed herein. In some embodiments, the conjugate and/or polymer comprises, consists essentially of, or consists of a first peptide comprising, consisting essentially of, or consisting of the amino acid sequence of SEQ ID NO: 2, SEQ ID NO: 3, and/or SEQ ID NO: 4, a modified peptide thereof, or a fragment thereof, conjugated to a second peptide comprising, consisting essentially of, or consisting of the amino acid sequence of SEQ ID NO: 11 or SEQ ID NO: 12, a modified peptide thereof, or a fragment thereof. In some embodiments, the first peptide is directly conjugated to the second peptide or the first and second peptides are indirectly conjugated to each other via a linker. In some embodiments, the linker is a peptide linker comprising 1-9 amino acids, wherein in some embodiments the 1-9 amino acids are each individually selected from the group consisting of glycine and serine. In some embodiments, the conjugate and/or polymer comprises, consists essentially of, or consists of an amino acid sequence selected from the group consisting of (SEQ ID NO: 13)
VPLSRTVRTVRCTCISIGGGPESKAIKNLLKAVSKERSKRSP, (SEQ ID NO: 14)
PESKAIKNLLKAVSKERSKRSPGGGVPLSRTVRCTCISI, (SEQ ID NO: 15)
LSRTVRTVRCTCISIGGGPESKAIKNLLKAVSKERSKRSP, (SEQ ID NO: 16)
PESKAIKNLLKAVSKERSKRSPGGGLSRTVRCTCISI, (SEQ ID NO: 17)
RTVRCTCISIGGGPESKAIKNLLKAVSKERSKRSP, (SEQ ID NO: 18)
PESKAIKNLLKAVSKERSKRSPGGGRTVRCTCI, (SEQ ID NO: 19)
VPLSRTVRCTCISIGGGKNLLKAVSKERSKRSP, (SEQ ID NO: 20)
KNLLKAVSKERSKRSPGGGVPLSRTVRCTCISI, (SEQ ID NO: 21)
LSRTVRCTCISIGGGKNLLKAVSKERSKRSP, (SEQ ID NO: 22)
KNLLKAVSKERSKRSPGGGLSRTVRCTCISI, (SEQ ID NO: 23)
RTVRCTCISIGGGKNLLKAVSKERSKRSP, (SEQ ID NO: 24)
KNLLKAVSKERSKRSPGGGRTVRCTCI, a modified peptide thereof, or a fragment thereof. In some embodiments, the conjugate and/or polymer is polymer-functionalized, encapsulated in a particle, embedded in and/or on a solid support, optionally wherein the peptide is formulated for release from the solid support, impregnated in a dressing, optionally wherein the peptide is formulated for release from the dressing, and/or is formulated for use in a nebulizer, for topical administration, and/or for systemic administration.

The presently disclosed subject matter also relates in some embodiments to conjugates and/or polymers comprising one or more peptides comprising, consisting essentially of, or consisting of the amino acid sequence RTVRCTCI (SEQ ID NO: 2); one or more peptides comprising, consisting essentially of, or consisting of the amino acid sequence LSRTVRCTCISI (SEQ ID NO: 3); one or more peptides comprising, consisting essentially of, or consisting of the amino acid sequence VPLSRTVRCTCISI (SEQ ID NO: 4); one or more peptides comprising, consisting essentially of, or consisting of the amino acid sequence PESKAI-KNLLKAVSKERSKRSP (SEQ ID NO: 11); a modified peptide thereof; a fragment thereof; or any combination thereof, wherein each peptide present in the conjugate is covalently linked to at least one other peptide via a non-peptide linker, a peptide linker, or a cysteine-cysteine linkage. In some embodiments, the conjugate and/or polymer comprises a branched conjugate and/or polymer, a flanking conjugate and/or polymer, a single conjugate and/or polymer, a linear conjugate and/or polymer, a bottlebrush conjugate and/or polymer, or any combination thereof. In some embodiments, the conjugate and/or polymer is polymer-functionalized, encapsulated in a particle, embedded in and/or on a solid support, optionally wherein the conjugate and/or polymer is formulated for release from the solid support, impregnated in a dressing, optionally wherein the conjugate and/or polymer is formulated for release from the dressing, and/or is formulated for use in a nebulizer, for topical administration, and/or for systemic administration.

The presently disclosed subject matter also relates in some embodiments to pharmaceutical compositions comprising, consisting essentially of, or consisting of the peptide, modified peptides, fragments, conjugates, and/or polymers disclosed herein, or any combination thereof, and a pharmaceutically acceptable carrier, diluent, or excipient. In some embodiments, the pharmaceutical composition is pharmaceutically acceptable for use in a human.

The presently disclosed subject matter also relates in some embodiments to medical devices comprising a support layer with an antibacterial agent embedded therein or associated therewith, wherein the antibacterial agent comprises a peptide, modified peptide, or fragment as disclosed herein, a conjugate as disclosed herein, a polymer as disclosed herein, or any combination thereof, optionally wherein the medical device is a wound dressing. In some embodiments, the peptide, modified peptide, fragment, conjugate, and/or polymer is encapsulated in a particle that is embedded in or associated with the support layer.

The presently disclosed subject matter also relates in some embodiments to methods for inhibiting the growth of and/or killing bacteria. In some embodiments, the methods comprise contacting a bacterium with an effective amount of an antibacterial agent selected from the group consisting of the a peptide, modified peptide, or fragment as disclosed herein, a conjugate as disclosed herein, a polymer as disclosed herein, or any combination thereof. In some embodiments, the bacterium is selected from the group consisting of *Enterococcus faecium, Staphylococcus aureus, Klebsiella pneumoniae, Acinetobacter baumannii, Pseudomonas aeruginosa*, members of the family Enterobacteriaceae, including but not limited to *Escherichia coli, Klebsiella* spp., *Enterobacter cloacae*, and *Serratia* spp.; sexually-transmitted bacteria such as but not limited to *Neisseria gonorrhoeae*; enteric pathogens such as but not limited to *Salmonella enterica* serovars such as but not limited to *Salmonella enterica* serovar *Typhi*, and *Shigella flexneri*; and biothreat agents such as but not limited to *Bacillus anthracis* in both vegetative and spore forms.

The presently disclosed subject matter also provides in some embodiments methods for recruiting immune cells to sites of infection in subjects. In some embodiments, the methods comprise administering to a subject in need thereof, optionally at the site of infection, a composition comprising a peptide comprising, consisting essentially of, or consisting of the amino acid sequence VPLSRTVRCTCISI (SEQ ID NO: 4), a modified peptide thereof, a fragment thereof, a conjugate thereof, a polymer thereof, and/or a composition comprising a peptide comprising, consisting essentially of, or consisting of the amino acid sequence LSRTVRCTCISI (SEQ ID NO: 3), a modified peptide thereof, a fragment thereof, a conjugate thereof, a polymer thereof, or any combination thereof.

The presently disclosed subject matter also provides in some embodiments methods for treating or preventing community and/or nosocomial infections in subjects. In some embodiments, the methods comprise administering to a subject in need thereof a composition comprising a peptide comprising, consisting essentially of, or consisting of the amino acid sequence, RTVRCTCI (SEQ ID NO: 2), the amino acid sequence LSRTVRCTCISI (SEQ ID NO: 3), the amino acid sequence VPLSRTVRCTCISI (SEQ ID NO: 4), a modified peptide thereof, a fragment thereof, a conjugate thereof, a polymer thereof, or a combination thereof.

The presently disclosed subject matter also provides methods for inducing a subject's immune system against a pathogen. In some embodiments, the methods comprise administering to the subject a composition comprising a peptide comprising, consisting essentially of, or consisting of the amino acid sequence, RTVRCTCI (SEQ ID NO: 2), the amino acid sequence LSRTVRCTCISI (SEQ ID NO: 3), the amino acid sequence VPLSRTVRCTCISI (SEQ ID NO: 4), a modified peptide thereof, a fragment thereof, a conjugate thereof, a polymer thereof, or a combination thereof.

In some embodiments, the presently disclosed subject matter also provides methods for treating bacterial infections present in a wound and/or a surgical site. In some embodiments, the method comprise contacting a wound and/or the surgical site with an effective amount of a composition comprising one or more peptides, each peptide comprising, consisting essentially of, or consisting of an amino acid sequence as set forth in SEQ ID NOs: 2-91, a modified peptide thereof, a fragment thereof. In some embodiments, the one or more peptides are present in a conjugate as disclosed herein. In some embodiments, the one or more peptides are present in a polymer as disclosed herein.

The presently disclosed subject matter also provides methods for treating pulmonary infections in subjects. In some embodiments, the methods comprise administering to a subject in need thereof an effective amount of a composition comprising one or more peptides, each peptide comprising, consisting essentially of, or consisting of an amino acid sequence as set forth in SEQ ID NOs: 2-91, a modified peptide thereof, a fragment thereof, a conjugate thereof, and/or a polymer thereof. In some embodiments, the composition is administered to the subject intranasally, by inhalation, optionally wherein the one or more peptides in the composition is/are aerosolized, or a combination thereof.

The presently disclosed subject matter also provides in some embodiments methods for treating or preventing systemic bacterial infections in subjects. In some embodiments, the methods comprise administering to a subject in need thereof an effective amount of a composition comprising one or more peptides, each peptide comprising, consisting essentially of, or consisting of an amino acid sequence as set forth in SEQ ID NOs: 2-91, a modified peptide thereof, or a fragment thereof. In some embodiments, the one or more peptides are present in a conjugate as disclosed herein.

The presently disclosed subject matter also relates in some embodiments to methods for inhibiting the growth of a biofilm, which can include reducing the presence of a biofilm on a surface. In some embodiments, the methods comprise contacting a bacterium, such as a bacterium in a biofilm or capable of forming a biofilm, with an effective amount of an antibacterial agent selected from the group consisting of a peptide, modified peptide, or fragment as disclosed herein, a conjugate as disclosed herein, or any combination thereof.

In some embodiments, the presently disclosed treatment and/or preventive methods relate to combination treatments. Thus, in some embodiments the presently disclosed methods further comprise administering to the subject a conventional antibiotic.

Accordingly, in some embodiments the presently disclosed subject matter relate to uses of the peptides, modified peptides, fragments thereof, conjugates thereof, and/or polymers thereof, and/or any combination thereof, for preventing or treating a bacterial infection.

Accordingly, it is an object of the presently disclosed subject matter to provide methods and compositions for treating and/or preventing infection by bacteria, in some embodiments MDR bacteria.

This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Figures, and Examples.

BRIEF DESCRIPTION OF THE FIGURES

FIG. 12A is a bar graph showing in vivo recruitment/infiltration of $CD45^+/CD3^+$ T lymphocytes was measured in peritoneal lavages collected 6 hours after intraperitoneal injection of saline alone or equimolar amounts of recombinant human CXCL10 (SEQ ID NO: 1), Peptide P1 (SEQ ID NO: 4), or peptide ΔVP (SEQ ID NO: 3) into C57BL/6 mice. T-cell counts from naïve animals are shown as a baseline control of immune-cell localization. Cellular infiltrates were quantified using flow cytometry. Data, expressed as absolute cell number, are the mean±SEM, n=4 male+4 female animal per group. FIG. 12B is a bar graph showing in vitro human T-cell migration in response to 25 nM hCXCL10 (SEQ ID NO: 1), or Peptide P5 (SEQ ID NO: 8), Peptide P1 (SEQ ID NO: 4), or Peptide D8 (SEQ ID NO: 2) was measured using the CHEMOTX® trans-well system (Neuro Probe, Inc., Gaithersburg, Maryland, United States of America). Data, expressed as chemotactic index (cells migrating to condition/cells migrating to buffer alone), are the mean±SEM, n=2 per Peptide. * $p<0.001$ and  $p<0.01$ as compared to saline-alone (FIG. 12A) or the Peptide P5 (SEQ ID NO: 8; FIG. 12B) control; ns=not significant.

FIG. 14A is a graph showing mortality among infected peptide- and saline-treated animals. Kaplan-Meier survival curves represent the combined mortality from 8 mice total per group. * $p<0.001$ as compared to saline controls. FIG. 14B is a series of photographs of wounds over the course of infection. Representative image sets from pairs of peptide- and saline-treated animals surviving through day 21 are shown. In peptide-treated wounds, bacterial infection was resolved and healing occurred. In contrast, the infected wounds of saline-treated mice deteriorated significantly, remaining heavily infected and unhealed at the end of observation. FIG. 14**C shows the results of wound swabs streaked onto lysogeny broth (LB) agar to assess bacterial burden at day 14 post-infection. No bacterial growth was observed for swabs taken from peptide-treated wounds; heavy growth was observed for those taken from saline-treated wounds.

BRIEF DESCRIPTION OF THE SEQUENCE LISTING

Figure 1:
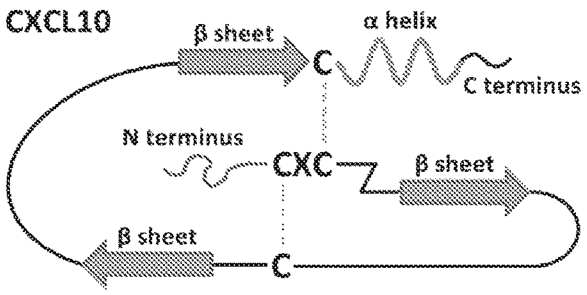
FIG. 1 is a structural representation of the human CXCL10 polypeptide. CXCL10 consists of an unstructured N-terminal region responsible for interaction with the cellular receptor CXCR3, three antiparallel β-sheets, and an amphipathic C-terminal α-helix. As disclosed herein, peptides derived from the N- or C-terminal regions of CXCL10 can mediate direct bactericidal effects against bacterial pathogens including MDR isolates thereof.

SEQ ID NO: 1 is the amino acid sequence of the mature form of a human CXCL10 (hCXCL10) polypeptide, and corresponds to amino acids 22-98 of Accession No. NP_001556.2 of the GENBANK® biosequence database.

SEQ ID NOs: 2-91 are the amino acid sequences of exemplary antibacterial peptides, conjugates, and/or polymers of the presently disclosed subject matter. It is understood that with respect to any of SEQ ID NOs: 2-91, one or more, in some embodiments all, amino acids can be L-amino acids, D-amino acids, or any combination thereof. In some embodiments of SEQ ID NOs: 2-91, all amino acids are D-amino acids.

More particularly:

SEQ ID NO: 2 is the amino acid sequence of a core eight amino acid peptide referred to herein as L8 when all amino acids are L-amino acids and D8 when all amino acids are D-amino acids that is derived from the N-terminus of SEQ ID NO: 1 and has been shown to have antibacterial activity.

SEQ ID NO: 3 is the amino acid sequence derived from the N-terminus of SEQ ID NO: 1 that has been shown to have antibacterial activity but reduced or absent immunomodulatory activity. This peptide is referred to herein as the ΔVP Peptide.

SEQ ID NO: 4 is the amino acid sequence derived from the N-terminus of SEQ ID NO: 1 that has been shown to have antibacterial activity and immunomodulatory activity. This peptide is referred to herein as Peptide P1.

SEQ ID NOs: 5-11 are the amino acid sequences of certain overlapping peptides derived from SEQ ID NO: 1 that together with SEQ ID NO: 4 span the entire sequence of SEQ ID NO: 1. SEQ ID NOs: 5-11 are referred to herein as Peptides P2-P6, P8, and P9, respectively.

SEQ ID NO: 12 is amino acid sequence derived from the C-terminus of SEQ ID NO: 1. It is a truncated version of SEQ ID NO: 11 (Peptide P9) that retains the activities of Peptide P9. It is thus a 16 amino acid "core" peptide having the functions associated with Peptide P9 and the C-terminus of hCXCL10.

SEQ ID NO: 13 is the amino acid sequence of an exemplary conjugate of the presently disclosed subject matter in which Peptide P1 (SEQ ID NO: 4) is conjugated to Peptide P9 (SEQ ID NO: 11) via a tri-glycine linker. It is referred to herein alternatively as P1-GGG-P9 or P55.

SEQ ID NO: 14 is the amino acid sequence of another exemplary conjugate of the presently disclosed subject matter in which Peptide P9 (SEQ ID NO: 11) is conjugated to Peptide P1 (SEQ ID NO: 4) via a tri-glycine linker. It is referred to herein alternatively as P9-GGG-P1 or P59.

SEQ ID NO: 15 is the amino acid sequence of another exemplary conjugate of the presently disclosed subject matter in which Peptide ΔVP (SEQ ID NO: 3) is conjugated to Peptide P9 (SEQ ID NO: 11) via a tri-glycine linker.

SEQ ID NO: 16 is the amino acid sequence of another exemplary conjugate of the presently disclosed subject matter in which Peptide P9 (SEQ ID NO: 11) is conjugated to Peptide ΔVP (SEQ ID NO: 3) via a tri-glycine linker.

SEQ ID NO: 17 is the amino acid sequence of another exemplary conjugate of the presently disclosed subject matter in which Peptide L8 (SEQ ID NO: 2) is conjugated to Peptide P9 (SEQ ID NO: 11) via a tri-glycine linker. In an all L-amino acid form it is referred to herein as P68.

SEQ ID NO: 18 is the amino acid sequence of another exemplary conjugate of the presently disclosed subject matter in which Peptide P9 (SEQ ID NO: 11) is conjugated to Peptide L8 (SEQ ID NO: 2) via a tri-glycine linker.

SEQ ID NO: 19 is the amino acid sequence of another exemplary conjugate of the presently disclosed subject matter in which Peptide P1 (SEQ ID NO: 4) is conjugated to the C-terminal core peptide of SEQ ID NO: 12 via a tri-glycine linker.

SEQ ID NO: 20 is the amino acid sequence of another exemplary conjugate of the presently disclosed subject matter in which the C-terminal core peptide of SEQ ID NO: 12 is conjugated to Peptide P1 (SEQ ID NO: 4) via a tri-glycine linker.

SEQ ID NO: 21 is the amino acid sequence of another exemplary conjugate of the presently disclosed subject matter in which Peptide ΔVP (SEQ ID NO: 3) is conjugated to the C-terminal core peptide of SEQ ID NO: 12 via a tri-glycine linker.

SEQ ID NO: 22 is the amino acid sequence of another exemplary conjugate of the presently disclosed subject matter in which the C-terminal core peptide of SEQ ID NO: 12 is conjugated to Peptide ΔVP (SEQ ID NO: 3) via a tri-glycine linker.

SEQ ID NO: 23 is the amino acid sequence of another exemplary conjugate of the presently disclosed subject matter in which Peptide L8 (SEQ ID NO: 2) is conjugated to the C-terminal core peptide of SEQ ID NO: 12 via a tri-glycine linker.

SEQ ID NO: 24 is the amino acid sequence of another exemplary conjugate of the presently disclosed subject matter in which the C-terminal core peptide of SEQ ID NO: 12 is conjugated to Peptide L8 (SEQ ID NO: 2) via a tri-glycine linker.

SEQ ID NOs: 25-32 are the amino acid sequences of alanine scanned variants of Peptide L8 (SEQ ID NO: 2). In each of SEQ ID NOs: 25-32, one amino acid starting at the N-terminus was replaced with an alanine.

SEQ ID NOs: 33-46 are the amino acid sequences of alanine scanned variants of Peptide P1 (SEQ ID NO: 4). In each of SEQ ID NOs: 33-46, one amino acid starting at the N-terminus was replaced with an alanine.

SEQ ID NOs: 47-66 are the amino acid sequences of alanine scanned variants of Peptide P9 (SEQ ID NO: 11). In each of SEQ ID NOs: 47-66, one amino acid starting at the N-terminus was replaced with an alanine.

SEQ ID NOs: 67-85 are the amino acid sequences of amino acid position 2 substitution variants of Peptide L8 (SEQ ID NO: 2). In each of SEQ ID NOs: 67-85, amino acid 2 was substituted with one of the other 19 amino acids.

SEQ ID NO: 86 is the amino acid sequence of a scrambled variant of Peptide P1 (SEQ ID NO: 4).

SEQ ID NO: 87 is the amino acid sequence of another exemplary conjugate of the presently disclosed subject matter in which three copies of Peptide L8 (SEQ ID NO: 2) are concatemerized in head-to-tail configuration. This Peptide is referred to herein as L8-L8-L8.

SEQ ID NO: 88 is the amino acid sequence of another exemplary conjugate of the presently disclosed subject matter in which three copies of Peptide L8 (SEQ ID NO: 2) are concatemerized in head-to-tail configuration but with a tri-glycine linker between each concatemer. This Peptide is referred to herein as L8-GGG-L8-GGG-L8.

SEQ ID NO: 89 is the amino acid sequence of a variant of Peptide P9 (SEQ ID NO: 11) in which amino acids 8 and 12 were substituted with 2-(4-pentenyl) alanine (pA). In some embodiments, this peptide can be "stapled" via interaction between the two 2-(4-pentenyl) alanine (pA) residues, which in some embodiments can stabilize the α-helix structure of the peptide.

SEQ ID NO: 90 is the amino acid sequence of a variant of Peptide P9 (SEQ ID NO: 11) in which amino acids 5 and 12 were substituted with 2-(4-pentenyl) alanine (pA). In some embodiments, this peptide can be "stapled" via interaction between the two 2-(4-pentenyl) alanine (pA) residues, which in some embodiments can stabilize the α-helix structure of the peptide.

SEQ ID NO: 91 is the amino acid sequence of a retro version of Peptide P9 in which the amino acid sequence of Peptide P9 (SEQ ID NO: 11) has been reversed. This peptide is referred to herein as P9 retro.

SEQ ID NO: 92 is the amino acid sequence of a linear polymer of three (3) copies of SEQ ID NO: 2 without linkers.

SEQ ID NO: 93 is the amino acid sequence of a linear polymer of three (3) copies of SEQ ID NO: 2 with GGG tripeptide linkers between each monomer of SEQ ID NO: 2.

SEQ ID NO: 94 is the amino acid sequence of a polymer of SEQ ID NO: 2 linked to SEQ ID NO: 11.

DETAILED DESCRIPTION

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. General Considerations

Chemokines are chemotactic cytokines that are important regulators of leukocyte-mediated inflammation and immunity in response to a variety of diseases and infectious processes in the host. Chemokines are a superfamily of homologous 8-10 kDa heparin-binding proteins, originally identified for their role in mediating leukocyte recruitment. The four major families of chemokine ligands are classified on the basis of a conserved amino acid sequence at their amino terminus, and are designated CXC, CC, C, and CX3C sub-families (where "X" is a non-conserved amino acid residue).

The interferon-inducible ($ELR^-$) CXC chemokines are one of the largest families of chemokines, and each member of this group contains four cysteine residues. Most chemokines are small proteins (8-10 kDa in size), have a net positive charge at neutral pH, and share considerable amino acid sequence homology. Structurally, the defining feature of the CXC chemokine family is a motif of four conserved cysteine residues, the first two of which are separated by a non-conserved amino acid, thus constituting the Cys-X-Cys or 'CXC' motif. This family is further subdivided on the basis of the presence or absence of another three amino acid sequence, glutamic acid-leucine-arginine (the 'ELR' motif), immediately proximal to the CXC sequence. The ELR-positive ($ELR^+$) CXC chemokines, which include IL-8/CXCL8, are potent neutrophil chemoattractants and promote angiogenesis. Among the ELR-negative (ELR) CXC chemokines, CXCL9, CXCL10, and CXCL11 are potently induced by both type 1 and type 2 interferons (IFN-$\alpha$/$\beta$ and IFN-$\gamma$, respectively). These Interferon-inducible (ELR) CXC chemokines are generated by a variety of cell types including monocytes, macrophages, lymphocytes, and epithelial cells, and are extremely potent chemoattractants for recruiting mononuclear leukocytes, including activated Th1 CD4 T cells, natural killer (NK) cells, NKT cells, and dendritic cells to sites of inflammation and inhibiting angiogenesis.

The chemokine receptors are a family of related receptors that are expressed on the surface of all leukocytes as well as other cells. The shared receptor for CXCL9, CXCL10, and CXCL11 is CXCR3. Through their interaction with CXCR3, the ligands CXCL9, CXCL10, and CXCL11 are the major recruiters of specific leukocytes, including CD4 T cells, NK cells, and myeloid dendritic cells. Importantly, this chemokine ligand-receptor system is at the core of a positive feedback loop escalating Th1 immunity, whereby cytokines such as interleukin (IL)-12 and IL-18 (released by myeloid accessory cells) activate local NK cells to produce IFN-$\gamma$, thereby inducing the generation of CXCL9, CXCL10, and CXCL11, which then recruits CXCR3-expressing cells that act as a further source of IFN-$\gamma$, which then induces further production of CXCL9, CXCL10, and CXCL11. Consistent with the importance of these interferon-inducible (ELR-) CXC chemokines in promoting Th1-mediated immunity, CXCR3 and its ligands have been documented to play a critical role in host defense against many microorganisms, including viruses, *Mycobacterium tuberculosis*, bacteria, and protozoa.

Independent of their role in CXCR3-dependent leukocyte recruitment, CXCL9, CXCL10, and CXCL11 have recently been found to display direct antimicrobial properties that resemble those of defensins. These antimicrobial effects were first demonstrated in 2001 against *Escherichia coli* and *Listeria monocytogenes*. Subsequently, an increasing number of chemokines have been shown to have antimicrobial activity against various strains of bacteria and fungi, including *Escherichia coli, Staphylococcus aureus, Candida albicans*, and *Cryptococcus neoformans*.

The presently disclosed subject matter leverages the ELR-negative (ELR) CXC chemokine/chemokine receptor system to provide compositions and methods for treating and/or preventing bacterial infections, including but not limited to infections with MDR bacteria.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. Mention of techniques employed herein are intended to refer to the techniques as commonly understood in the art, including variations on those techniques or substitutions of equivalent techniques that would be apparent to one of skill in the art. Thus, unless defined otherwise, all technical and scientific terms and any acronyms used herein have the same meanings as commonly understood by one of ordinary skill in the art in the field of the presently disclosed subject matter. Although any compositions, methods, kits, and means for communicating information similar or equivalent to those described herein can be used to practice the presently disclosed subject matter, particular compositions, methods, kits, and means for communicating information are described herein. It is understood that the particular compositions, methods, kits, and means for communicating information described herein are exemplary only and the presently disclosed subject matter is not intended to be limited to just those embodiments.

Following long-standing patent law convention, the terms "a", "an", and "the" refer to "one or more" when used in this application, including the claims. Thus, in some embodiments the phrase "a peptide" refers to one or more peptides.

The term "about", as used herein to refer to a measurable value such as an amount of weight, time, dose (e.g., therapeutic dose), etc., is meant to encompass in some embodiments variations of +20%, in some embodiments ±10%, in some embodiments ±5%, in some embodiments ±1%, in some embodiments ±0.5%, in some embodiments ±0.1%, and in some embodiments ±0.01% from the specified amount, as such variations are appropriate to perform the disclosed methods.

As used herein, the term "and/or" when used in the context of a list of entities, refers to the entities being present singly or in any and every possible combination and subcombination. Thus, for example, the phrase "A, B, C, and/or D" includes A, B, C, and D individually, but also includes any and all combinations and subcombinations of A, B, C, and D. It is further understood that for each instance wherein multiple possible options are listed for a given element (i.e., for all "Markush Groups" and similar listings of optional components for any element), in some embodiments the optional components can be present singly or in any combination or subcombination of the optional components. It is implicit in these forms of lists that each and every combination and subcombination is envisioned and that each such combination or subcombination has not been listed simply merely for convenience. Additionally, it is further understood that all recitations of "or" are to be interpreted as "and/or" unless the context clearly requires that listed components be considered only in the alternative (e.g., if the components would be mutually exclusive in a given context and/or could not be employed in combination with each other).

A disease or disorder is "alleviated" if the severity of a symptom of the disease, condition, or disorder, or the frequency with which such a symptom is experienced by a subject, or both, are reduced by any measurable criterion. In some embodiments, a disease or disorder is "alleviated" if the severity of a symptom of the disease, condition, or disorder, or the frequency with which such a symptom is experienced by a subject, or both, are reduced to a condition that would be considered to be normal (i.e., absent).

As used herein, the term "subject" refers to an individual (e.g., human, animal, or other organism) to be treated by the methods or compositions of the present invention. Subjects include, but are not limited to, mammals (e.g., murines, simians, equines, bovines, porcines, canines, felines, and the like), and includes humans. In the context of the invention, the term "subject" generally refers to an individual who will receive or who has received treatment for a condition characterized by the presence of bacteria (e.g., *Bacillus anthracis* (e.g., in any stage of its growth cycle), or in anticipation of possible exposure to bacteria. As used herein, the terms "subject" and "patient" are used interchangeably, unless otherwise noted.

As used herein, the terms "neutralize" and "neutralization" when used in reference to bacterial cells or spores (e.g., *B. anthracis* cells and spores) refers to a reduction in the ability of the spores to germinate and/or cells to proliferate.

As used herein the term "bacterial spore" or "spore" is used to refer to any dormant, non-reproductive, but viable structure produced by some bacteria (e.g., *Bacillus* and *Clostridium*) in response to adverse environmental conditions.

As used herein, the term "treating a surface" refers to the act of exposing a surface to one or more compositions of the present invention. Methods of treating a surface include, but are not limited to, spraying, misting, submerging, wiping, and coating. Surfaces include organic surfaces (e.g., food products, surfaces of animals, skin, etc.) and inorganic surfaces (e.g., medical devices, countertops, instruments, articles of commerce, clothing, etc.).

As used herein, the terms "effective amount" and "therapeutically effective amount" are used interchangeably and refer to the amount that provides a therapeutic effect, e.g., an amount of a composition that is effective to treat or prevent pathological conditions, including signs and/or symptoms of disease, associated with a pathogenic organism infection (e.g., spore germination, bacterial growth, toxin production, etc.) in a subject.

The terms "bacteria" and "bacterium" refer to all prokaryotic organisms, including those within all of the phyla in the Kingdom Procaryotae. As used herein, the term "microorganism" refers to any species or type of microorganism, including but not limited to, bacteria, archaea, fungi, protozoans, *mycoplasma*, and parasitic organisms.

As used herein the term "colonization" refers to the presence of bacteria in a subject that are either not found in healthy subjects, or the presence of an abnormal quantity and/or location of bacteria in a subject relative to a healthy patient.

The term "stationary growth phase" as used herein defines the growth characteristics of a given population of microorganisms. During a stationary growth phase the population of bacteria remains stable with the rate of bacterial division being approximately equal to the rate of bacterial death. This can be due to increased generation time of the bacteria. Accordingly "stationary phase bacteria" are bacteria that are in a stationary growth phase. "Exponential phase bacteria" are bacteria that are rapidly proliferating and the population is rapidly expanding, typically the number of bacteria increases at an exponential rate.

As used herein a "multidrug-resistant" (or "MDR") microorganism or bacteria is an organism that has an enhanced ability, relative to non-resistant strains, to resist distinct drugs or chemicals (of a wide variety of structure and function) targeted at eradicating the organism. Typically, the term refers to resistance to at least 3 classes of antibiotics.

Chemokines are small proteins secreted by cells that have the ability to induce directed chemotaxis in responsive cells. As used herein the term "interferon-inducible (ELR) CXC chemokine" refers to a chemokine protein, or corresponding peptidomimetic, having a motif of four conserved cysteine residues, the first two of which are separated by a non-conserved amino acid (thus constituting the Cys-X-Cys or 'CXC' motif; see FIG. 1) and devoid of a three amino acid sequence, glutamic acid-leucine-arginine (the 'ELR' motif), immediately proximal to the CXC sequence. Examples of interferon-inducible (ELR) CXC chemokines include human CXCL9, murine CXCL9, human CXCL10 (SEQ ID NO: 1), murine CXCL10, human CXCL11, and murine CXCL11. CXCL9, CXCL10, and CXCL11 are potently induced by both type 1 and type 2 interferons (IFN-α/β and IFN-γ, respectively).

As used herein, the term "adjuvant" as used herein refers to an agent which enhances the pharmaceutical effect of another agent.

The expression "amino acid" as used herein is meant to include both natural and synthetic amino acids, and both D- and L-amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage can be present or absent in the peptides of the invention.

The term "amino acid" is used interchangeably with "amino acid residue", and can refer to a free amino acid and to an amino acid residue of a peptide. It will be apparent from the context in which the term is used whether it refers to a free amino acid or a residue of a peptide.

The term "antibody", as used herein, refers to an immunoglobulin molecule which is able to specifically bind to a specific epitope on an antigen. Antibodies can be derived from natural sources or from recombinant sources and can be intact immunoglobulins or immunoreactive portions of intact immunoglobulins (for example, a fragment or derivative of an antibody that includes an antigen-binding site or a paratope). Antibodies are typically tetramers of immunoglobulin molecules. The antibodies in the present invention can exist in a variety of forms including, for example, polyclonal antibodies, monoclonal antibodies, Fv, Fab and F (ab) 2, as well as single chain antibodies and humanized antibodies (see e.g., Harlow & Lane (1999) *Using Antibodies: A Laboratory Manual*, Cold Spring Harbor Laboratory Press, Cold Spring Harbor, New York, United States of America; Harlow & Lane (1988) *Antibodies: A Laboratory Manual*, Cold Spring Harbor Laboratory Press, Cold Spring Harbor, New York, United States of America; Houston et al. (1988) Proc Natl Acad Sci USA 85:5879-5883; Bird et al. (1988) Science 242:423-426; each of which is incorporated herein by reference in its entirety).

The term "synthetic antibody" as used herein refers to an antibody which is generated using recombinant DNA technology, such as, for example, an antibody expressed by a bacteriophage or a host cell. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antimicrobial agent", as used herein, refers to any entity that exhibits antimicrobial activity, i.e. the ability to inhibit the growth of and/or kill bacteria, including for example the ability to inhibit growth or reduce viability of bacteria by at least about 30%, at least about 40%, at least about 50%, at least about 60%, at least about 70% or more than 70%, as compared to bacteria not exposed to the antimicrobial agent. The antimicrobial agent can exert its effect either directly or indirectly and can be selected from a library of diverse compounds, including for example antibiotics. For example, various antimicrobial agents act, inter alia, by interfering with (1) cell wall synthesis, (2) plasma membrane integrity, (3) nucleic acid synthesis, (4) ribosomal function, and (5) folate synthesis. One of ordinary skill in the art will appreciate that a number of "antimicrobial susceptibility" tests can be used to determine the efficacy of a candidate antimicrobial agent.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (see e.g., U.S. Pat. No. 5,034,506 to Summerton and Weller; Nielsen et al. (1991) Science 254:1497-1500). The term "antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence can be complementary to regulatory sequences specified on the coding strand of a DNA molecule encoding a protein, which regulatory sequences control expression of the coding sequences.

As used herein, the term "biologically active fragments" or "bioactive fragment" of a polypeptide encompasses natural or synthetic portions of the full-length protein that are capable of specific binding to their natural ligand or of performing the function of the protein.

A "pathogenic" cell is a cell which, when present in a tissue, causes or contributes to a disease or disorder in the animal in which the tissue is located (or from which the tissue was obtained).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T", is complementary to the sequence "T-C-A."

The term "complex", as used herein in reference to proteins, refers to binding or interaction of two or more proteins. Complex formation or interaction can include such things as binding, changes in tertiary structure, and modification of one protein by another, such as phosphorylation.

A "compound", as used herein, refers to any type of substance or agent that is commonly considered a chemical, drug, or a candidate for use as a drug, as well as combinations and mixtures of the above. The term compound further encompasses molecules such as peptides and nucleic acids.

As used herein, the term "cytokine" refers to an intercellular signaling molecule, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that can be produced from another compound of similar structure in one or more steps, as in replacement of H by an alkyl, acyl, or amino group. Similarly, a "derivative" of a peptide (or of a polypeptide) is a compound that can be produced from or has a biological activity similar to a peptide (or a polypeptide) but that differs in the primary amino acid sequence of the peptide (or the polypeptide) to some degree. By way of example and not limitation, a derivative of a subject peptide of the presently disclosed subject matter is a peptide that has a similar although not identical primary amino acid sequence as the subject peptide (for example, has one or more amino acid substitutions) and/or that has one or more other modifications (e.g., N-terminal, C-terminal, and/or internal modifications) as compared to the subject peptide. Thus, the term "derivative" compasses the term "modified peptide" and vice versa, in the context of peptides. In some embodiments, a derivative of a peptide is a C-terminal amidated peptide.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA can include introns.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid of the amino acid sequence, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

The terms "formula" and "structure" are used interchangeably herein.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J Mol Biol 215:403-410) are available for determining sequence identity.

In some embodiments, "identity" can be expressed as a "percent identity". As used herein, the phrase "percent identity" in the context of two nucleic acid or polypeptide sequences, refers to two or more sequences or subsequences that have in some embodiments 60%, in some embodiments 70%, in some embodiments 75%, in some embodiments 80%, in some embodiments 85%, in some embodiments 90%, in some embodiments 92%, in some embodiments 94%, in some embodiments 95%, in some embodiments 96%, in some embodiments 97%, in some embodiments 98%, in some embodiments 99%, and in some embodiments 100% nucleotide or amino acid residue identity, respectively, when compared and aligned for maximum correspondence, as measured using one of the following sequence comparison algorithms or by visual inspection. The percent identity exists in some embodiments over a region of the sequences that is at least about 50 residues in length, in some embodiments over a region of at least about 100 residues, and in some embodiments, the percent identity exists over at least about 150 residues. In some embodiments, the percent identity exists over the entire length of the sequences.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm disclosed in Smith & Waterman (1981) 2 Adv Appl Math 482-489; by the homology alignment algorithm disclosed in Needleman & Wunsch (1970) 48 J Mol Biol 443-453; by the search for similarity method disclosed in Pearson Pearson & Lipman (1988) Proc Natl Acad Sci USA 85:2444-2448; by computerized implementations of these algorithms (GAP, BESTFIT, FASTA, and TFASTA in the GCG® WISCONSIN PACKAGER, available from Accelrys, Inc., San Diego, California, United States of America), or by visual inspection. See generally, Altschul et al. (1990) 215 J Mol Biol 403-410; Ausubel et al. (2002) Short Protocols in Molecular Biology, Fifth ed. Wiley, New York, New York, United States of America; and Ausubel et al. (2003) Current Protocols in Molecular Biology, John Wylie & Sons, Inc, New York, New York, United States of America.

One example of an algorithm that is suitable for determining percent sequence identity and sequence similarity is the BLAST algorithm, which is described in Altschul et al. (1990) 215 J Mol Biol 403-410. Software for performing BLAST analysis is publicly available through the website of the National Center for Biotechnology Information. This algorithm involves first identifying high scoring sequence pairs (HSPs) by identifying short words of length W in the query sequence, which either match or satisfy some positive valued threshold score T when aligned with a word of the same length in a database sequence. T is referred to as the neighborhood word score threshold. See generally, Altschul et al. (1990) 215 J Mol Biol 403-410. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix. See Henikoff & Henikoff (1992) 89 Proc Natl Acad Sci USA 10915-10919.

In addition to calculating percent sequence identity, the BLAST algorithm also performs a statistical analysis of the similarity between two sequences (see e.g., Karlin & Altschul (1993) 90 Proc Natl Acad Sci USA 5873-5877). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

The term "inhibit", as used herein, refers to the ability of a compound or any agent to reduce or impede a described function or pathway. For example, inhibition can be by at least 10%, by at least 25%, by at least 50%, by at least 75%, by at least 80%, by at least 85%, by at least 90%, by at least 95%, by at least 97%, by at least 99%, or more.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound invention or be shipped together with a container which contains the identified compound. Alternatively, the instructional material can be shipped separately from the container with the intention that the instructional material and the compound be used cooperatively by the recipient.

An "isolated" compound/moiety is a compound/moeity that has been removed from components naturally associated with the compound/moiety. For example, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "modulate", as used herein, refers to changing the level of an activity, function, or process. The term "modulate" encompasses both inhibiting and stimulating an activity, function, or process.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in an animal. In some embodiments, a pharmaceutically acceptable carrier is pharmaceutically acceptable for use in a human.

The term "polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides (e.g., a polypeptide of in some embodiments at least 50 amino acids, in some embodiments at least 75 amino acids, in some embodiments at least 100 amino acids, in some embodiments at least 200 amino acids, in some embodiments at least 300 amino acids, in some embodiments at least 500 amino acids, and in some embodiments more than 500 amino acids).

A peptide encompasses a sequence of 2 or more amino acids wherein the amino acids are naturally occurring or synthetic (non-naturally occurring) amino acids.

The term "linked" or like terms refers to a connection between two entities. The linkage can comprise a covalent, ionic, or hydrogen bond or other interaction that binds two compounds or substances to one another.

As used herein the term "peptidomimetic" refers to a chemical compound having a structure that is different from the general structure of an existing peptide, but that functions in a manner similar to the existing peptide, e.g., by mimicking the biological activity of that peptide. The term "modified peptide" encompasses a peptidomimetic. Peptidomimetics typically comprise naturally-occurring amino acids and/or unnatural amino acids, but can also comprise modifications to the peptide backbone. For example, a peptidomimetic can include one or more of the following modifications:

1. Peptides wherein one or more of the peptidyl —C(O)NR— linkages (bonds) have been replaced by a non-peptidyl linkage such as a —$CH_2$-carbamate linkage (—$CH_2OC(O)NR$—), a phosphonate linkage, a —$CH_2$-sulfonamide (—$CH_2$—$S(O)_2NR$—) linkage, a urea (—NHC(O)NH—) linkage, a —$CH_2$-secondary amine linkage, an azapeptide bond (CO substituted by NH), or an ester bond (e.g., depsipeptides, wherein one or more of the amide (—CONHR—) bonds are replaced by ester (COOR) bonds) or with an alkylated peptidyl linkage (—C(O)NR—) wherein R is $C_1$-$C_6$ alkyl;
2. Peptides wherein the N-terminus is derivatized to a —NRR1 group, to a —NRC(O)R group, to a —NRC(O)OR group, to a —NRS$(O)_2$R group, to a —NHC(O)NHR group where R and R1 are hydrogen or $C_1$-$C_6$ alkyl with the proviso that R and R1 are not both hydrogen;
3. Peptides wherein the C terminus is derivatized to —C(O)R2 where R2 is selected from the group consisting of $C_1$-$C_6$ alkoxy, and —NR3R4 where R3 and R4 are independently selected from the group consisting of hydrogen and $C_1$-$C_4$ alkyl;
4. Modification of a sequence of naturally-occurring amino acids with the insertion or substitution of a non-peptide moiety, e.g., a retroinverso fragment.

The term "permeability", as used herein, refers to transit of fluid, cell, or debris between or through cells and tissues.

A "sample", as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds", as used herein, is meant a compound which recognizes and binds a specific protein, but does not substantially recognize or bind other molecules in a sample, or it means binding between two or more proteins as in part of a cellular regulatory process, where said proteins do not substantially recognize or bind other proteins in a sample.

The term "standard", as used herein, refers to something used for comparison. For example, it can be a known standard agent or compound which is administered or added to a control sample and used for comparing results when measuring said compound in a test sample. Standard can also refer to an "internal standard", such as an agent or compound which is added at known amounts to a sample and is useful in determining such things as purification or recovery rates when a sample is processed or subjected to purification or extraction procedures before a marker of interest is measured.

The term "symptom", as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

As used herein an "amino acid modification" refers in some embodiments to a substitution, addition, or deletion of an amino acid, and includes substitution with, or addition of, any of the 20 amino acids commonly found in human proteins, as well as unusual or non-naturally occurring amino acids such as but not limited to D-amino acids. Commercial sources of unusual amino acids include Sigma-Aldrich (Milwaukee, Wisconsin, United States of America), ChemPep Inc. (Miami, Florida, United States of America), and Genzyme Pharmaceuticals (Cambridge, Massachusetts, United States of America). Unusual amino acids can be purchased from commercial suppliers, synthesized de novo, or chemically modified or derivatized from naturally occurring amino acids. Amino acid modifications include linkage of an amino acid to a conjugate moiety, such as a hydrophilic polymer, acylation, alkylation, and/or other chemical derivatization of an amino acid. The term "modified peptide" encompasses any amino acid modification as described herein.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substitutions can be designed based on, for example, the model of Dayhoff et al. (in *Atlas of Protein Sequence and Structure* 1978, National Biomedical Research Foundation, Washington D.C., United States of America).

In some embodiments, an amino acid substitution is a conservative amino acid substitution. As used herein, the term "conservative amino acid substitution" is defined in some embodiments as exchanges within one of the following five groups:

I. Small aliphatic, nonpolar or slightly polar residues: Ala, Ser, Thr, Pro, Gly;

II. Polar, charged residues and their amides: Asp, Asn, Glu, Gln, His, Arg, Lys;

III. Large, aliphatic, nonpolar residues: Met Leu, Ile, Val, Cys

IV. Large, aromatic residues: Phe, Tyr, Trp

Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al. (1990) Science 247:1306-1310.

For example, the hydropathic index of amino acids may be considered (Kyte & Doolittle (1982) J Mol Biol 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle (1982) J Mol Biol 157:105-132), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

tryptophan (−3.4). Replacement of amino acids with others of similar hydrophilicity is preferred.

Other considerations include the size of the amino acid side chain. For example, in some embodiments an amino acid with a compact side chain, such as glycine or serine, would not be replaced with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet, or reverse turn secondary structure has been determined and is known in the art (see e.g., Chou & Fasman (1974) Biochemistry 13:222-245; Chou & Fasman (1978) Ann Rev Biochem 47:251-276; Chou & Fasman (1979) Biophys J 26:367-384).

Based on such considerations and extensive empirical study, tables of conservative amino acid substitutions have been constructed and are known in the art. By way of example and not limitation, the following substitutions can be made: arginine and lysine; glutamate and aspartate; serine and threonine; glutamine and asparagine; and valine, leucine, and isoleucine. Alternatively, Table 1 lists exemplary conservative amino acid substitutions.

TABLE 1

Exemplary Conservative Amino Acid Substitutions

| Amino Acid | Possible Substitution(s) | Amino Acid | Possible Substitution(s) |
|---|---|---|---|
| Ala (A) | Leu, Ile, Val | Leu (L) | Val, Met, Ala, Phe, Ile |
| Arg (R) | Gln, Asn, Lys | Lys (K) | Gln, Asn, Arg |
| Asn (N) | His, Asp, Lys, Arg, Gln | Met (M) | Phe, Ile, Leu |
| Asp (D) | Asn, Glu | Phe (F) | Leu, Val, Ile, Ala, Tyr |
| Cys (C) | Ala, Ser | Pro (P) | Ala |
| Gln (Q) | Glu, Asn | Ser (S) | Thr |
| Glu (E) | Gln, Asp | Thr (T) | Ser |
| Gly (G) | Ala | Trp (W) | Phe, Tyr |
| His (H) | Asn, Gln, Lys, Arg | Tyr (Y) | Trp, Phe, Thr, Ser |
| Ile (I) | Val, Met, Ala, Phe, Leu | Val (V) | Ile, Leu, Met, Phe, Ala |

In some embodiments, another consideration for amino acid substitutions include whether or not the residue is located in the interior of a protein or is solvent exposed. For interior residues, conservative substitutions can include in some embodiments: Asp and Asn; Ser and Thr; Ser and Ala; Thr and Ala; Ala and Gly; Ile and Val; Val and Leu; Leu and Ile; Leu and Met; Phe and Tyr; Tyr and Trp. For solvent exposed residues, conservative substitutions can include in some embodiments: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, the Dayhoff matrix, the Grantham matrix, the Mclachlan matrix, the Doolittle matrix, the Henikoff matrix, the Miyata matrix, the Fitch matrix, the Jones matrix, the Rao matrix, the Levin matrix, and the Risler matrix (summarized in, for example, Johnson & Overington (1993) J Mol Biol 233:716-738; see also the PROWL resource available at the website of The Rockefeller University, New York, New York, United States of America).

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

III. Compositions

III.A. Peptides, Modified Peptides, Conjugates, and Polymers Thereof

In some embodiments, the presently disclosed subject matter relates to peptides, modified peptides, conjugates thereof, polymers thereof, and combinations thereof that have antimicrobial activity. The peptides of the presently disclosed subject matter were initially identified by consideration of the structure of the human CXCL10 (hCXCL10) gene product. CXCL10 is a small, 10 kiloDalton (kDa) protein that is produced by a variety of cells. The basic structure of hCXCL10 polypeptide is depicted in FIG. 1.

As shown in FIG. 1, hCXCL10 is characterized by several domains, including an N-terminus that is involved with interacting with the CXCR3 receptor to regulate chemotaxis and other immunomodulatory effects and a C-terminus that broadly resembles antimicrobial peptides in that it comprises a cationic amphipathic helix structure. Between the N-terminus and the C-terminus there are three B sheets as well as the CXC domain, the two cysteines of which create cysteine-cysteine disulfide bridges, the first with a cysteine present between the first and second β sheets and the second with a cysteine present just N-terminal to the a helix present in the C-terminal domain. hCXC10 itself has potent activity in recruiting immune cells to sites of inflammation by virtue of its N-terminal domain interacting with CXCR3, as well as other bioregulatory activities. Full-length hCXCL10 also has direct antimicrobial activity against a variety of pathogens such as but not limited to *Bacillus anthracis, Acinetobacter baumannii*, and New Delhi metallo-β-lactamase (NDM) producing *Klebsiella* penumoniae.

As disclosed herein, peptides derived from the N-terminus of hCXCL10 have been identified as having antimicrobial activity, including bactericidal activity. Thus, in some embodiments the presently disclosed subject matter relates to peptides comprising, consisting essentially of, or consisting of the amino acid sequence RTVRCTCI (SEQ ID NO: 2), or modified peptides thereof, or fragments thereof. Exemplary such peptides include peptides comprising, consisting essentially of, or consisting of the amino acid sequence LSRTVRCTCISI (SEQ ID NO: 3) and VPLSRTVRCTCISI (SEQ ID NO: 4), or modified peptides thereof, or fragments thereof.

Additionally, the alanine scanning and truncation experiments disclosed herein below in the EXAMPLES indicated that various amino acid positions in these peptides could be substituted with other amino acids. For example, amino acids 1, 2, and 6 of RTVRCTCI (SEQ ID NO: 2) can be substituted with other amino acids and/or otherwise modified as described herein. Such modifications can include in some embodiments amino acid substitutions, which in some embodiments can be conservative amino acid substitutions, in some embodiments substitutions with unnatural amino acids, D-amino acids, and/or peptidomimetics, or any combination thereof.

Peptides derived from the C-terminus of hCXCL10 have also been identified as having antimicrobial activity, including antibacterial activity. Thus, in some embodiments the presently disclosed subject matter also relates to peptides comprising, consisting essentially of, or consisting of the amino acid sequence PESKAIKNLLKAVSKERSKRSP (SEQ ID NO: 11) or KNLLKAVSKERSKRSP (SEQ ID NO: 12), or modified peptides thereof, or fragments thereof. With respect to both of these peptide sequences, various amino acid positions, including amino acids 2, 3, 8, 14, 16, 18, 21, and 22 of PESKAIKNLLKAVSKERSKRSP (SEQ ID NO: 11) can be substituted with other amino acids and/or otherwise modified as described herein. Such modifications can include in some embodiments amino acid substitutions, which in some embodiments can be conservative amino acid substitutions, in some embodiments substitutions with unnatural amino acids, D-amino acids, and/or peptidomimetics, or any combination thereof.

Figure 18:
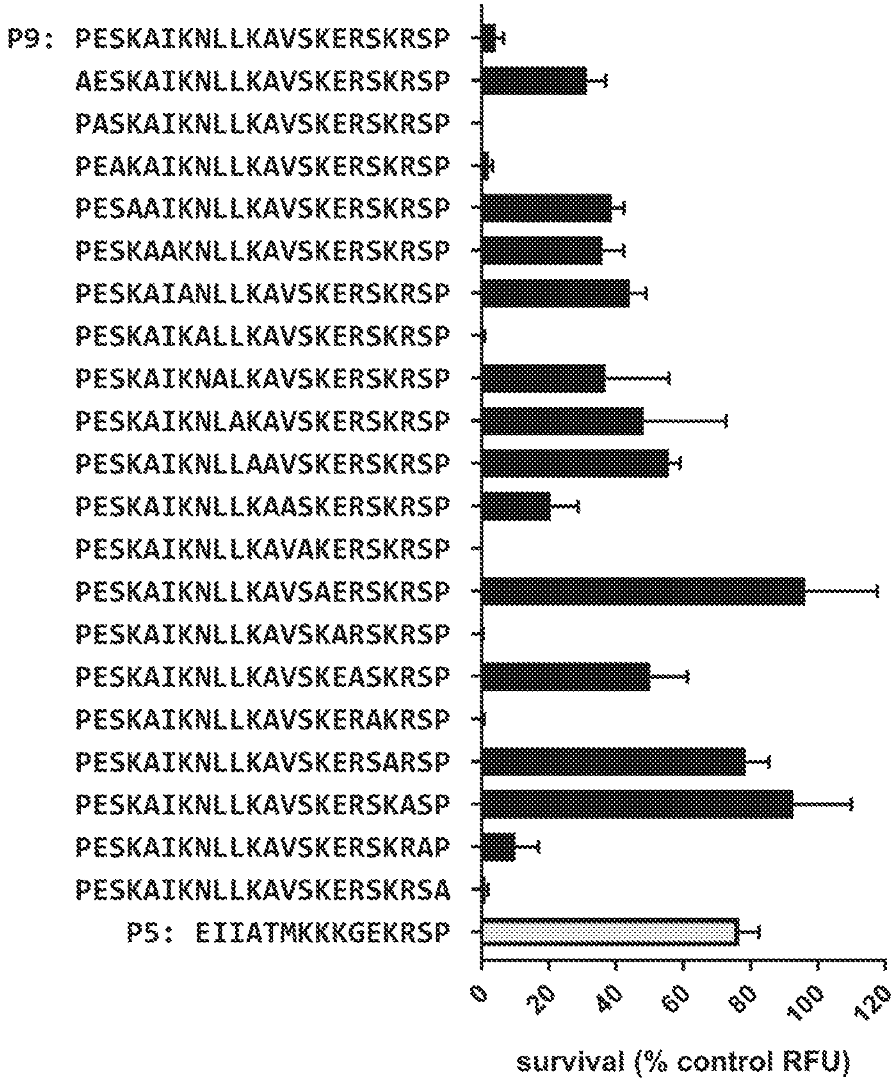
FIG. 18 is a bar graph showing bactericidal activities of Peptide P9 alanine scan variants (SEQ ID NOs: 11 and 47-66) against CRE *K. pneumoniae*. CRE *K. pneumoniae* ($2.5\times10^5$ cfu/ml) were treated with 5.6 μM of the indicated Peptide P9 alanine scan variants (SEQ ID NOs: 11 and 47-66) in 10 mM potassium phosphate buffer supplemented with 1% Tryptic Soy Broth for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.

In some embodiments, alanine scans are available for PESKAIKNLLKAVSKERSKRSP (SEQ ID NO: 11). The alanine scan was used to modify the malleable position 8 and to make a conservative substitution at alanine residue 12 with an alkenyl derivative of alanine, namely, 2-(4-pentenyl) alanine, and then the alkene groups at positions 8 and 12 were coupled/stapled. Thus, a modified peptide in accordance with the presently disclosed subject matter includes a coupled peptide or a stapled peptide. Data shows the increased activity of the alkene-modified peptide and even more so in the stapled peptide. See FIG. 18. Further, the first 6 amino acids present in PESKAIKNLLKAVSKERSKRSP (SEQ ID NO: 11) can be removed one by one while still retaining activity; removing all 6 gives KNLLKAVSKERSKRSP (SEQ ID NO: 12). Further truncations are also provided, including from the other end (such as the two end residues based on the alanine scan).

In some embodiments, one, two, three, four, five, six, seven, eight, nine, ten, or more amino acids of a peptide of the presently disclosed subject matter are D-amino acids, and in some embodiments all of the amino acids of a peptide of the presently disclosed subject matter are D-amino acids. Acceptable amino acid substitutions are those that do not negatively affect the anti-bacterial ability of the D-amino acid-containing peptide. A peptide having an identical amino acid sequence to that found within a parent peptide but in which all L-amino acids have been substituted with all D-amino acids is also referred to as an "inverso" compounds. For example, if a parent peptide is Arg-Thr-Val, the inverso form is D-Arg-D-Thr-D-Val.

Figure 23:
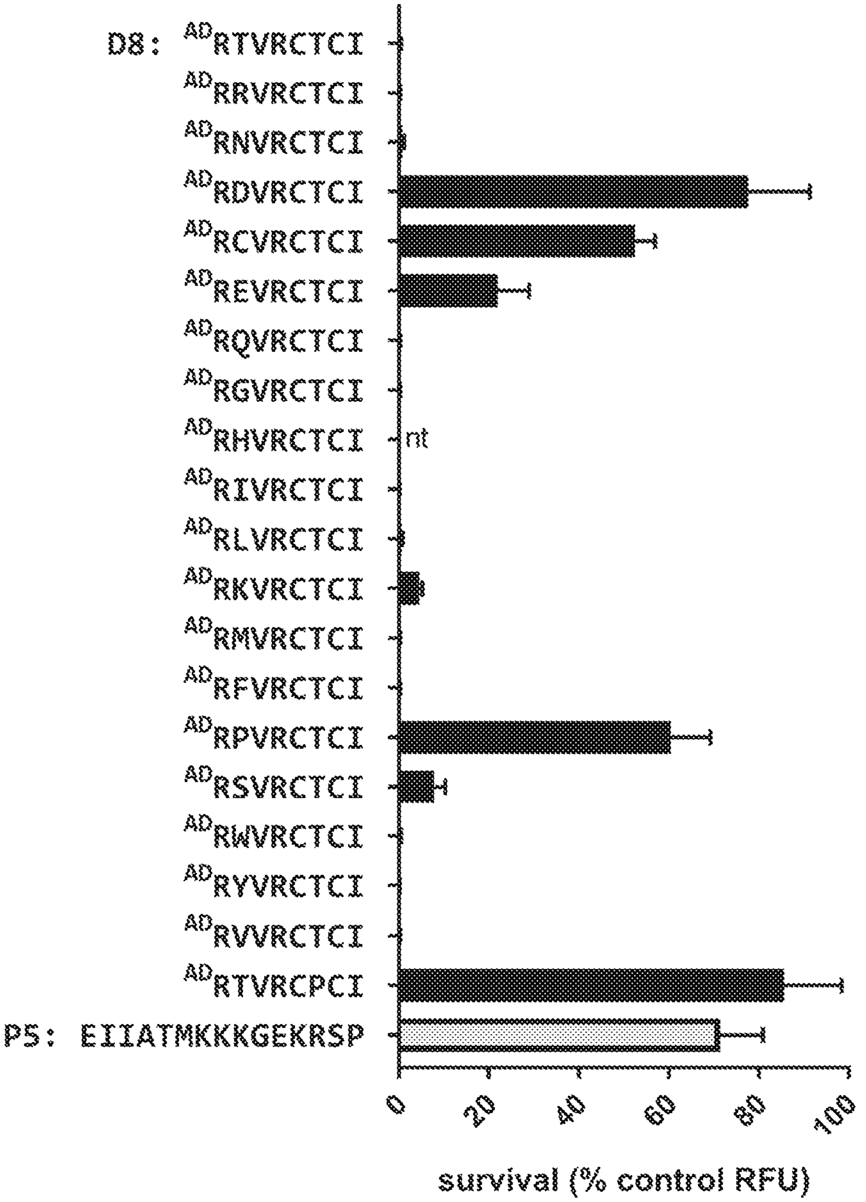
FIG. 23 is a bar graph showing bactericidal activities of Peptide D8, position 2 substitution variants (SEQ ID NOs: 2 and 67-85) against CRE *K. pneumoniae*. CRE *K. pneumoniae* ($2.5\times10^5$ cfu/ml) were treated with 50 μM of Peptide D8 (SEQ ID NO: 2) or Peptide D8 amino acid position 2 substitution variants (SEQ ID NOs: 67-85) in which the threonine at position 2 of Peptide D8 (SEQ ID NO: 2) was substituted with other D-amino acids. Bacterial survival was assessed in RPMI/HEPES using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.

In some embodiments, the malleable positions within the presently disclosed sequences were determined by testing the activity of a series of peptide sequences in which alanine is substituted for each residue, e.g., ATVRCTCI (position 1; SEQ ID NO: 25), RAVRCTCI (position 2; SEQ ID NO: 26), etc. (see also SEQ ID NOs: 2732) The alanine scan establishes the malleability of these positions in more than just a conservative way (e.g. in positions 1 and 2, alanine is quite different from highly charged arginine and hydroxyl-bearing threonine, but still functional and thus included as a modified peptide in accordance with the presently disclosed subject matter). See FIGS. 15-18, 21, and 22. For Peptide D8 (SEQ ID NO: 2 with all D-amino acids), a replacement scan (FIG. 23) substituted the threonine at position 2 with other D-amino acids (see SEQ ID NOs: 67-85). Characterization of specific substitutions at other positions and in other peptides provides substitutions, or combinations thereof, that enhance peptide activity or advantageous pharmaceutical properties (e.g. solubility, stability, etc.).

Figure 20:
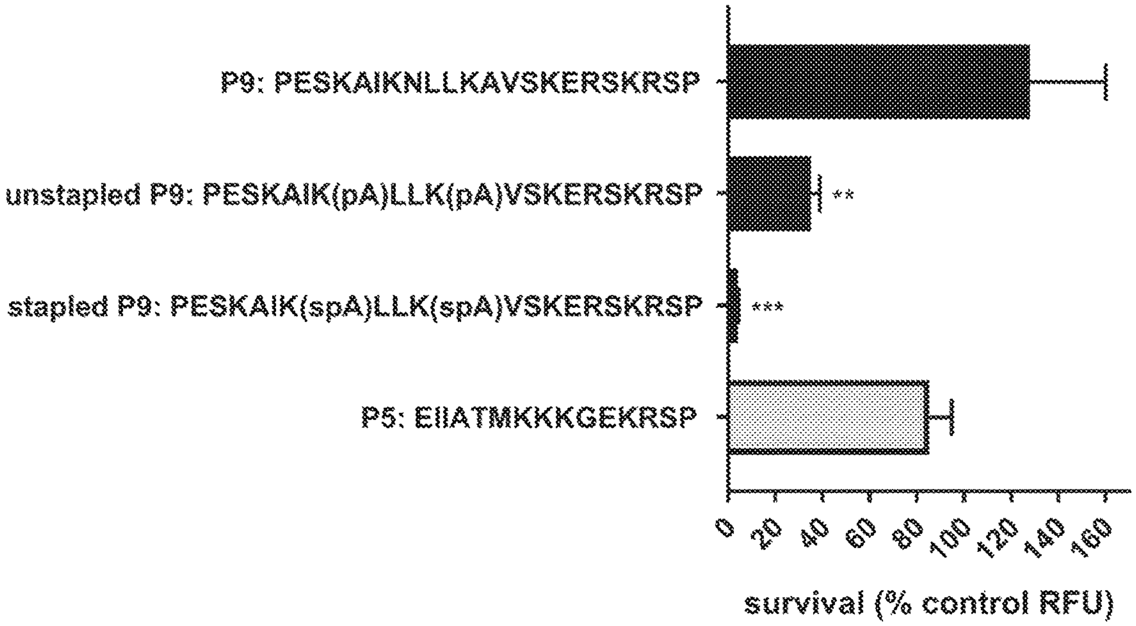
FIG. 20 is a bar graph showing bactericidal activities of unstapled and stapled Peptide P9 variants (SEQ ID NO: 89). CRE *K. pneumoniae* ($2.5\times10^5$ cfu/ml) were treated with 50 μM Peptide P9 (SEQ ID NO: 11), an unstapled variant containing 2-(4-pentenyl) alanine (pA; SEQ ID NO: 89), or a stapled variant (SEQ ID NO: 89) in which the alkene groups of the pA residues were coupled in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.
Figure 21:
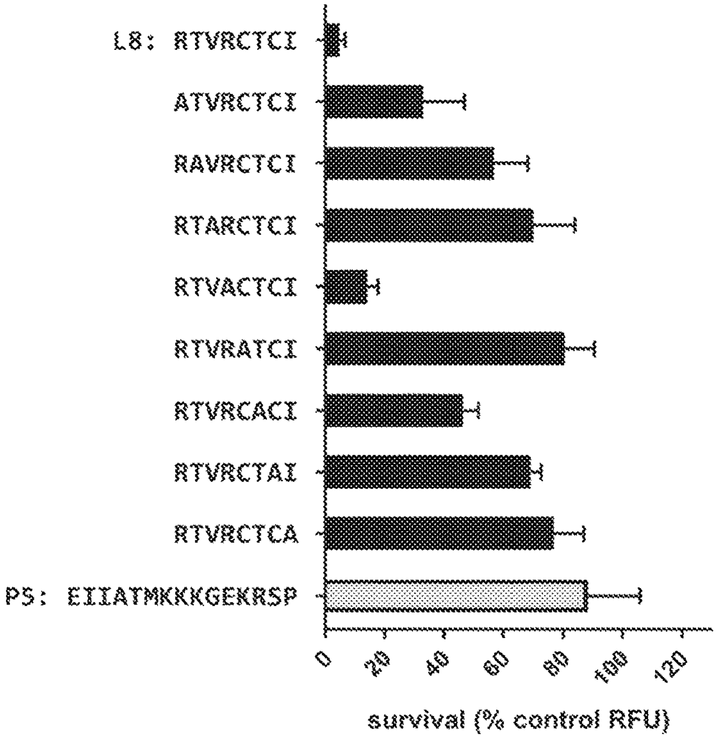
FIG. 21 is a bar graph showing bactericidal activities of Peptide L8 alanine scan variants (SEQ ID NOs: 2 and 25-32) against CRE *K. pneumoniae*. CRE *K. pneumoniae* ($2.5\times10^5$ cfu/ml) were treated with 50 μM of the indicated Peptide L8 alanine scan variants (SEQ ID NOs: 2 and 25-32) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.
Figure 22:
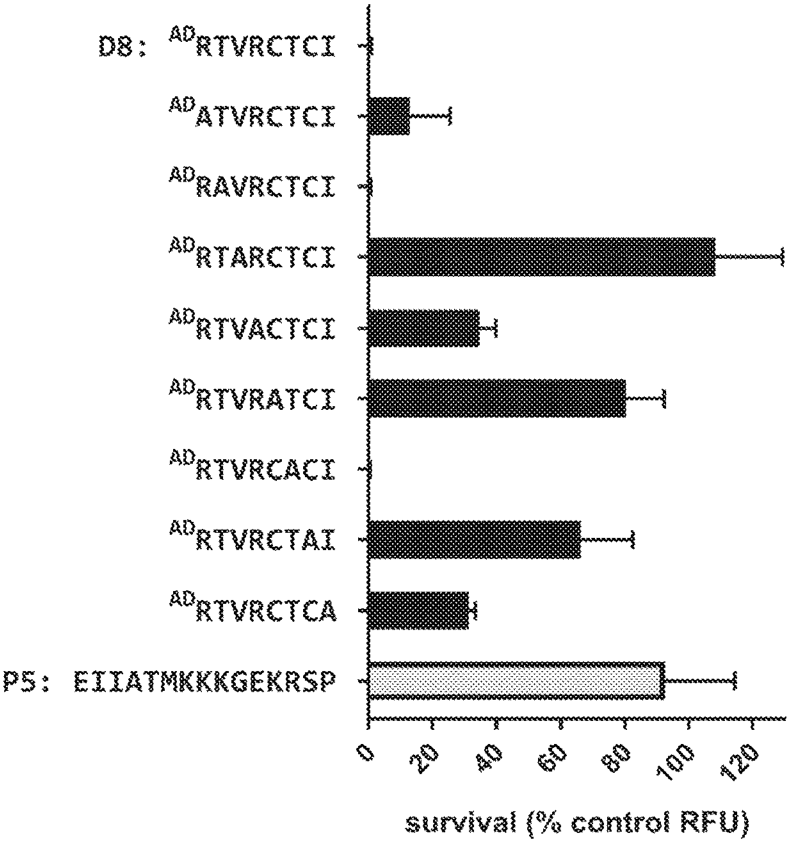
FIG. 22 is a bar graph showing bactericidal activities of Peptide D8 D-alanine scan variants (SEQ ID NOs: 2 and 25-32) against CRE *K. pneumoniae*. CRE *K. pneumoniae* ($2.5\times10^5$ cfu/ml) were treated with 50 μM of the indicated Peptide D8 D-alanine scan variants (SEQ ID NOs: 2 and 25-32) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide. AD: Peptide includes only D-amino acids.

In some embodiments, a modified peptide comprises a stapled sequence. By way of example and not limitation, the alkenyl residue can be named as (pA) for 2-(4-pentenyl) alanine is PESKAIK(pA)LLK(pA)VSKERSKRSP (SEQ ID NO: 89) and the stapled version, with the residues having the staples named as 'spA' PESKAIK(spA)LLK(spA)VSKERSKRSP (SEQ ID NO: 89). Since staples can also be constructed across 6 amino acids rather1 than just 3, the sequences PESK(pA)IKNLLK(pA)VSKERSKRSP (SEQ ID NO: 90) and PESK(spA)IKNLLK(spA)VSKERSKRSP (SEQ ID NO: 90) are also provided. See FIG. 20.

In some embodiments, a peptide of the presently disclosed subject matter is a retro-inverso isomer of another peptide. As used herein, the term "retro-inverso isomer" refers a peptide in which the sequence of the amino acids is reversed as compared to the sequence of another peptide and all L-amino acids are replaced with D-amino acids. For example, if a parent peptide is Arg-Thr-Val, the retro-inverso form is D-Val-D-Thr-D-Arg. Compared to the parent peptide, a retro-inverso peptide has a reversed backbone while retaining substantially the original spatial conformation of the side chains, resulting in a retro-inverso isomer with a topology that closely resembles the parent peptide (see Goodman el al. (1981) *Perspectives in Peptide Chemistry* pages 283-294. See also U.S. Pat. No. 4,522,752 for a further description of retro-inverso peptides.

In some embodiments, the peptides of the presently disclosed subject matter have bactericidal and/or bacteriostatic activity against various bacteria. Exemplary bacteria for which the presently disclosed peptides have antibacterial activity include, but are not limited to *Enterococcus faecium, Staphylococcus aureus, Klebsiella pneumoniae, Acinetobacter baumannii, Pseudomonas aeruginosa*, members of the family Enterobacteriaceae, including but not limited to *Escherichia coli, Klebsiella* spp., *Enterobacter cloacae*, and *Serratia* spp.; sexually-transmitted bacteria such as but not limited to *Neisseria gonorrhoeae*; enteric pathogens such as but not limited to serovars of *Salmonella enterica*, including but not limited to *Salmonella enterica* serovar *Typhi*, and *Shigella flexneri*; and biothreat agents such as but not limited to *Bacillus anthracis* in both vegetative and spore forms. In some embodiments, the peptides of the presently disclosed subject matter have antibacterial activity against a multi-drug-resistant (MDR) strain of a given bacterium. Exemplary non-limiting MDR bacteria for which the presently disclosed peptides have antibacterial activity include MDR strains of *Enterococcus faecium, Staphylococcus aureus, Klebsiella pneumoniae, Acinetobacter baumannii, Pseudomonas aeruginosa, Salmonella enterica*, optionally MDR serovars of *Salmonella enterica* such as but not limited to *Salmonella enterica* serovar *Typhi*, and *Shigella flexneri.*

The presently disclosed subject matter also provides in some embodiments conjugates and polymers comprising one or more of the peptides of the presently disclosed subject matter conjugated to a second active agent. In some embodiments, the second active agent is itself a peptide of the presently disclosed subject matter. By way of example and not limitation, a conjugate peptide of the presently disclosed subject matter can comprise, consist essentially of, or consist of the amino acid sequence RTVRCTCI (SEQ ID NO: 2), LSRTVRCTCISI (SEQ ID NO: 3), or VPLSRTVRCTCISI (SEQ ID NO: 4), or modified peptides thereof, or fragments thereof, conjugated to the amino acid sequence PESKAIKNLLKAVSKERSKRSP (SEQ ID NO: 11) or KNLLKAVSKERSKRSP (SEQ ID NO: 12), or modified peptides thereof, or fragments thereof.

Thus, in some embodiments the presently disclosed subject matter relates to a conjugate or polymer comprising a first peptide comprising, consisting essentially of, or consisting of the amino acid sequence of SEQ ID NO: 2, SEQ ID NO: 3, and/or SEQ ID NO: 4, or modified peptides thereof, or fragments thereof, conjugated to a second peptide comprising, consisting essentially of, or consisting of the amino acid sequence of SEQ ID NO: 11 or SEQ ID NO: 12, or modified peptides thereof, or fragments thereof. In some embodiments, the first peptide is directly conjugated to the second peptide or the first and second peptides are indirectly conjugated to each other via a linker. In some embodiments, the linker is a peptide linker, optionally a peptide of 1-9 amino acids, further optionally wherein the 1-9 amino acids are each individually selected from the group consisting of glycine and serine. In some embodiments, the conjugate or polymer comprises, consists essentially of, or consists of an amino acid sequence selected from the group consisting of (SEQ ID NO: 13)
VPLSRTVRTVRCTCISIGGGPESKAIKNLLKAVSKERSKRSP, (SEQ ID NO: 14)
PESKAIKNLLKAVSKERSKRSPGGGVPLSRTVRCTCISI, (SEQ ID NO: 15)
LSRTVRTVRCTCISIGGGPESKAIKNLLKAVSKERSKRSP, (SEQ ID NO: 16)
PESKAIKNLLKAVSKERSKRSPGGGLSRTVRCTCISI, (SEQ ID NO: 17)
RTVRCTCISIGGGPESKAIKNLLKAVSKERSKRSP, (SEQ ID NO: 18)
PESKAIKNLLKAVSKERSKRSPGGGRTVRCTCI, (SEQ ID NO: 19)
VPLSRTVRCTCISIGGGKNLLKAVSKERSKRSP, (SEQ ID NO: 20)
KNLLKAVSKERSKRSPGGGVPLSRTVRCTCISI, (SEQ ID NO: 21)
LSRTVRCTCISIGGGKNLLKAVSKERSKRSP, (SEQ ID NO: 22)
KNLLKAVSKERSKRSPGGGLSRTVRCTCISI, (SEQ ID NO: 23)
RTVRCTCISIGGGKNLLKAVSKERSKRSP, (SEQ ID NO: 24)
KNLLKAVSKERSKRSPGGGRTVRCTCI, or modified peptides thereof, or fragments thereof, or combinations thereof.

In some embodiments, a conjugate or polymer of the presently disclosed subject matter comprises one or more peptides comprising, consisting essentially of, or consisting of the amino acid sequence RTVRCTCI (SEQ ID NO: 2); one or more peptides comprising, consisting essentially of, or consisting of the amino acid sequence LSRTVRCTCISI (SEQ ID NO: 3); one or more peptides comprising, consisting essentially of, or consisting of the amino acid sequence VPLSRTVRCTCISI (SEQ ID NO: 4); one or more peptides comprising, consisting essentially of, or consisting of the amino acid sequence PESKAIKNLLKAVSKERSKRSP (SEQ ID NO: 11); or modified peptides thereof, or fragments thereof, or any combination thereof, wherein each peptide present in the conjugate is covalently linked to at least one other peptide via a non-peptide linker, a peptide linker, or a cysteine-cysteine linkage. In some embodiments, the conjugate or polymer comprises a branched conjugate, a flanking conjugate, a single conjugate, a linear polymer, a bottlebrush polymer, or any combination thereof.

In some embodiments, a conjugate or polymer comprises a peptide conjugated to the chain end of linear (or branched) poly(ethylene glycol) PEG or another hydrophilic polymer (e.g. poly(2-methacryloyoxyethyl phosphorylcholine)), and incorporated as 'combs'/pendent groups on a poly(methacrylate) or poly(methacrylamide) backbone. For the latter architecture, a polymerizable hydrophilic group (examples include oligoethylene glycol methacrylate, 2-methacryloyloxyethyl phosphoryl choline, and sulfobetaine methacrylate/sulfobetaine methacrylamide) is copolymerized with a polymerizable methacrylamide-terminated peptide (where the peptide bears a methacrylamide unit at the N terminus, accomplished by capping the peptide with a tri-glycine spacer, followed by methacrylic anhydride). In the copolymers, both the polymer molecular weight and the amounts of peptide and hydrophilic monomers can be varied. In some embodiments, controlled radical polymerizations—mainly reversible addition fragmentation chain transfer (RAFT) polymerization—are used—but these monomers are also amenable to atom transfer radical polymerization and conventional radical polymerization In some embodiments, a bottlebrush (e.g., a polymer of pendant polymer chains) or comb polymer approach is employed. Such an approach can employ poly(methacrylamide). In this polymer, one peptide or multiple types of peptides are conjugated at the N-terminal amine via a tri-glycine linker, followed by a methacrylamide groups (prepared by adding 3 glycines, followed by reaction of the N-terminal amine with methacrylic anhydride). These methacrylamides are polymerizable, and upon polymerization, result in a comb-type/bottlebrush polymethacrylamide in which peptides pendent to the main polymethacrylamide backbone like bristles on a bottlebrush. Combinations of peptides included within the same polymer bottlebrush are envisioned to be one peptide from (SEQ ID NOs: 2-4) and another from (SEQ ID NOs: 11 and 12), or combinations of D- and L-peptides. In these bottle brushes, some fraction of the chains can be dye labelled (e.g. by appending rhodamine B on a lysine side chain). In some embodiments, attachment/conjugation to the same polymer is employed.

In some embodiments, peptides in accordance with the presently disclosed subject matter can be combined into one construct by terminating both with a methacrylamide, then incorporating them at different ratios into copolymers. Similarly D- and L-versions of the peptides in accordance with the presently disclosed subject matter can be incorporated at different ratios into poly(methacrylate)s/poly(methacrylamide) s. This approach falls under the "indirect conjugation" strategy—but having them both on the same polymer is different than a simpler linear linker.

In some embodiments of a "polymer functionalized" approach, the peptide can be conjugated to the chain end of linear (or branched) poly(ethylene glycol) PEG or another hydrophilic polymer (e.g., poly(2-methacryloyoxyethyl phosphorylcholine)), and incorporated as 'combs'/pendent groups on a poly(methacrylate) or poly(methacrylamide) backbone. For the latter architecture, a polymerizable hydrophilic group (examples include oligoethylene glycol methacrylate, 2-methacryloyloxyethyl phosphoryl choline, and sulfobetaine methacrylate/sulfobetaine methacrylamide) is copolymerized with a polymerizable methacrylamide-terminated peptide (where the peptide bears a methacrylamide unit at the N terminus, accomplished by capping the peptide with a tri-glycine spacer, followed by methacrylic anhydride). In the copolymers, both the polymer molecular weight and the amounts of peptide and hydrophilic monomers can be varied. Controlled radical polymerizations— mainly reversible addition fragmentation chain transfer (RAFT) polymerization—are used—but these monomers are also amenable to atom transfer radical polymerization and conventional radical polymerization.

In some embodiments, N-terminal caps include acetyl groups (prepared by reaction of the N-terminal amine with acetic anhydride), tri-glycine-methacrylamide groups (prepared by adding 3 glycines, followed by reaction of the N-terminal amine with methacrylic anhydride), and dye-functionalized (prepared by reacting the N-terminal amine with rhodamine B).

In some embodiments, pegylation is possible at the N-terminus, or even by incorporating non-natural amino acids with PEGylated side chains (such non-natural amino acids incorporated into peptides).

In some embodiments, other modifications are provided. By way of example and not limitation, dyes are incorporated on peptide side chains or at the chain end, such as to facilitate pharmacokinetic studies. Such dyes range from rhodamine B (red) and fluorescein (green) to near-IR dyes that are compatible with animal imaging.

In some embodiments of a modified peptide in accordance with the presently disclosed subject matter, cysteine is replaced with selenocysteine: In some embodiments, conservative substitutions, like threonine to serine and valine to leucine/isoleucine are employed, but also substitutions with dyes are provided in the malleable positions to allow evaluation of in vivo half life, biodistribution, etc. An example of a dye-modified residue is a lysine residue where the amine side chain is functionalized with rhodamine B (bearing a carboxylic acid, therefore the same chemistry used to couple amino acids together is used on this side chain reaction). In some embodiments, cysteine residues are capped to abolish their reactivity and also tested for a balance of effects on peptide stability and function.

In some embodiments, a conjugate or polymer of the presently disclosed subject matter is polymer-functionalized, encapsulated in a particle, embedded in and/or on a solid support, impregnated on a dressing, and/or is formulated for use in a nebulizer, for topical administration, and/or for systemic administration. In some embodiments, the conjugate that is embedded/immobilized in and/or on a solid support such as a surface of a medical device such as a stent and/or impregnated on a dressing can be released from the solid support and/or the dressing, optionally wherein the release occurs when the solid support and/or the dressing comes in contact with a subject, optionally a bodily fluid, cell, tissue, or organ of a subject. In some embodiments, the release occurs over a pre-determined time frame. In some embodiments, the solid support and/or the dressing comprises a plurality of particles, wherein each particle is associated with, conjugated to, and/or encapsulates a peptide and/or a conjugate of the presently disclosed subject matter. In some embodiments, the plurality of particles are characterized by different release profiles, at least one of which is a slow-release profile, at least one of which is a fast-release profile, or combinations thereof (see e.g., U.S. Patent Application Publication No. 2011/0218140 for examples of slow-release and fast-release nanoparticles.

Thus, in some embodiments the presently disclosed subject matter relates to a wound dressing, wherein the wound dressing comprises a support layer with an antibacterial agent embedded therein or associated therewith. In some embodiments, the antibacterial agent comprises, consists essentially of, or consists of a peptide as disclosed herein, a conjugate as disclosed herein, a polymer as disclosed herein, or any combination thereof. In some embodiments, the peptide and/or conjugate is encapsulated in one or more particles that are embedded in or associated with the support layer. In some embodiments, some or all of the one or more particles are designed to release from the support layer when the dressing is in contact with a wound, and in some embodiments some or all of the one or more particles are designed to be retained in the support layer when the dressing is in contact with a wound.

III.B. Pharmaceutical Compositions

In some embodiments, the peptides and/or conjugates of the presently disclosed subject matter are present in a pharmaceutical composition. Thus, in some embodiments the presently disclosed subject matter relates to pharmaceutical compositions comprising, consisting essentially of, or consisting of one or more peptides as disclosed herein, one or more conjugates as disclosed herein, one or more polymers as disclosed herein, or any combination thereof, along with one or more pharmaceutically acceptable carriers, diluents, or excipients. In some embodiments, the presently disclosed pharmaceutical compositions are pharmaceutically acceptable for use in humans.

Thus, the disclosed pharmaceutical compositions can be employed by administration to a subject in need thereof. In some embodiments, the disclosed pharmaceutical compositions can be administered in vivo in a pharmaceutically acceptable carrier. By "pharmaceutically acceptable" is meant a material that is not biologically or otherwise undesirable, i.e., the material can be administered to a subject, along with a peptide composition of the presently disclosed subject matter, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution and/or in suspension (for example, incorporated into microparticles, liposomes, and/or cells.

The peptide, conjugate, and polymer compositions of the presently disclosed subject matter can be used therapeutically in combination with one or more pharmaceutically acceptable carriers.

Suitable carriers and their formulations are described in Remington et al. (1975) *Remington's Pharmaceutical Sciences,* 15th ed., Mack Pub. Co., Easton, Pennsylvania, United States of America. Typically, an appropriate amount of a pharmaceutically acceptable salt is used in the formulation to render the formulation isotonic. Examples of the pharmaceutically acceptable carrier include, but are not limited to, saline, Ringer's solution, and dextrose solution. The pH of the solution is in some embodiments from about 5 to about 8, and in some embodiments from about 7 to about 7.5. Further carriers include sustained release preparations such as semipermeable matrices of solid hydrophobic polymers containing the peptide compositions, which matrices are in the form of shaped articles, e.g., films, liposomes, or microparticles. It will be apparent to those persons skilled in the art that certain carriers can be selected depending upon, for instance, the route of administration and/or concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents, and the like, in addition to the molecule of choice. Pharmaceutical compositions can also include one or more active ingredients such as antimicrobial agents, anti-inflammatory agents, anesthetics, and the like.

The pharmaceutical composition can be administered in a number of ways depending on whether local or systemic treatment is desired, and on the area to be treated. Administration can occur topically (including ophthalmically, vaginally, rectally, intranasally), orally, by inhalation, or parenterally, for example by intravenous drip, subcutaneous, intraperitoneal or intramuscular injection. The disclosed peptide compositions can be administered in some embodiments topically, intravenously, intraperitoneally, intramuscularly, subcutaneously, intracavity, or transdermally.

Preparations for parenteral administration can include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids, and powders. Conventional pharmaceutical carriers, aqueous, powder or oily bases, thickeners, and the like can also be employed, as desired.

Compositions for oral administration include powders or granules, suspensions or solutions in water or non-aqueous media, capsules, sachets, or tablets. Thickeners, flavorings, diluents, emulsifiers, dispersing aids, or binders can in some embodiments also be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, or phosphoric acid and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl, and aryl amines and substituted ethanolamines.

IV. Methods for Using the Peptides, Modified Peptides, and Conjugates of the Presently Disclosed Subject Matter The presently disclosed subject matter compositions and pharmaceutical compositions can be employed for preventing and/or treating microorganismal infections either in vivo, ex vivo, or in vitro. Thus, in some embodiments the presently disclosed subject matter relates to methods for inhibiting the growth of and/or killing a bacterium. In some embodiments, the methods comprise contacting the bacterium with an effective amount of an antibacterial agent, wherein the antibacterial agent comprises, consists essentially of, or consists of a peptide as disclosed herein, a conjugate as disclosed herein, a polymer as disclosed herein, or any combination thereof.

Infection with both Gram-negative and Gram-positive bacteria can be treated and/or prevented using the compositions and methods of the presently disclosed subject matter. By way of example and not limitation, in some embodiments the bacterium is selected from the group consisting of *Enterococcus faecium, Staphylococcus aureus, Klebsiella pneumoniae, Acinetobacter baumannii, Pseudomonas aeruginosa*, members of the family Enterobacteriaceae, including but not limited to *Escherichia coli, Klebsiella* spp., *Enterobacter cloacae*, and *Serratia* spp.; sexually-transmitted bacteria such as but not limited to *Neisseria gonorrhoeae*; enteric pathogens such as but not limited to serovars of *Salmonella enterica*, including but not limited to *Salmonella enterica* serovar *Typhi*, and *Shigella flexneri*; and biothreat agents such as but not limited to *Bacillus anthracis* in both vegetative and spore forms. In some embodiments, the bacterium is selected from the group consisting of *Enterococcus* spp. including but not limited to *Enterococcus faecium* such as but not limited to vancomycin-resistant *E. faecium* (VRE), *Staphylococcus aureus* including but not limited to methicillin-resistant *S. aureus* (MRSA), *Klebsiella pneumoniae* including but not limited to multidrug resistant and carbapenem-resistant *K. pneumoniae, Acinetobacter* spp. including but not limited to multi-drug-resistant *Acinetobacter* spp., *Pseudomonas aeruginosa* including but not limited to multidrug-resistant *P. aeruginosa*, Enterobacteriaceae including but not limited to MDR and/or CRE *Escherichia coli, Klebsiella* spp., and *Serratia* spp., enteric pathogens including but not limited to multi-drug-resistant *Salmonella enterica* serovars such as serovar *Typhi* and multidrug-resistant *Shigella flexneri*, sexually-transmitted bacteria such as but not limited to *Neisseria gonorrhoeae*, and biothreat agents such as but not limited to both the vegetative and spore forms of *Bacillus anthracis.*

In some embodiments, the presently disclosed subject matter also relates to methods for treating bacterial infections present in wounds. In some embodiments, the methods comprise contacting the wound with an effective amount of a composition comprising one or more peptides, each peptide comprising, consisting essentially of, or consisting of an amino acid sequence as set forth in SEQ ID NOs: 2-91, or modified peptides thereof, or fragments thereof.

In some embodiments, an infection can be a pulmonary infection, and thus the presently disclosed subject matter related in some embodiments to methods for treating pulmonary infections in subjects by administering to a subject in need thereof an effective amount of a composition comprising one or more peptides, conjugates, and/or polymers, each peptide and/or conjugate and/or polymer comprising, consisting essentially of, or consisting of an amino acid sequence as set forth in SEQ ID NOs: 2-91, or modified peptides thereof, or fragments thereof. In some embodiments, the composition is administered to the subject intranasally, by inhalation, optionally wherein the one or more peptides in the composition is/are aerosolized, or any combination thereof.

The presently disclosed compositions can also be employed for treating or preventing systemic bacterial infections in subjects. In some embodiments, the methods comprise administering to a subject in need thereof an effective amount of a composition comprising one or more peptides and/or conjugates and/or polymers, each peptide and/or conjugate and/or polymer comprising, consisting essentially of, or consisting of an amino acid sequence as set forth in SEQ ID NOs: 2-91, or modified peptides thereof, or fragments thereof. The presently disclosed compositions can also be employed in a combination therapy in which the composition comprising one or more peptides and/or conjugates comprising, consisting essentially of, or consisting of an amino acid sequence as set forth in SEQ ID NOs: 2-91, or modified peptides thereof, or fragments thereof, is administered to the subject before, after, or concurrently with a second antibacterial therapy, which in some embodiments can involve the use of a conventional antibiotic. In some embodiments, the conventional antibiotic is selected from the group consisting of penicillins, cephalosporins, carbepenems, other beta-lactams antibiotics, aminoglycosides, macrolides, lincosamides, glycopeptides, tetracylines, chloramphenicol, quinolones, fucidins, sulfonamides, triinethoprims, rifamycins, oxalines, streptogramins, lipopeptides, ketolides, polyenes, azoles, and echinocandins.

Thus, in some embodiments the presently disclosed subject matter relates to any and all uses of the peptides disclosed herein, the conjugates disclosed herein, or any combination thereof for preventing or treating a bacterial infection.

As set forth herein, the N-terminal and C-terminal domains of the hCXCL10 polypeptide have different though complementary functions. The N-terminal domain is involved with interacting with the CXCR3 receptor to regulate chemotaxis and other immunomodulatory effects, and the C-terminus broadly resembles antimicrobial peptides in that it comprises a cationic amphipathic helix structure. As disclosed herein, those two biological activities can be separately maintained in some embodiments of the presently disclosed peptides and/or can be combined in some embodiments of the presently disclosed conjugates/polymers. These activities can thus also be taken advantage of with respect to certain uses of the presently disclosed peptides, conjugates, and/or polymers.

Therefore, in some embodiments the presently disclosed subject matter relates to methods for recruiting immune cells to a site of infection in a subject. In some embodiments, the methods comprise administering to a subject in need thereof, optionally at the site of infection, a composition comprising a peptide and/or a conjugate and/or polymer of the presently disclosed subject matter. In some embodiments, the composition comprises, consists essentially of, or consists of a peptide comprising, consisting essentially of, or consisting of the amino acid sequence LSRTVRCTCISI (SEQ ID NO: 3), the amino acid sequence VPLSRTVRCTCISI (SEQ ID NO: 4), or modified peptides thereof, or fragments thereof, or conjugates thereof. See FIG. 12. Thus, in some embodiments, peptides, conjugates, and polymers in accordance with the presently disclosed subject matter provide "full" immunomodulatory activity as compared to the full-length CXCL10 chemokine or provide moderated immune cell recruitment (FIG. 12).

Given that antibacterial activity of the presently disclosed subject matter peptides, conjugates, and/or polymers, the presently disclosed subject matter also provides in some embodiments methods for treating or preventing community and/or nosocomial infections in subjects. In some embodiments, the methods comprise administering to a subject at risk for developing and/or who has developed a community and/or nosocomial infection a composition of the presently disclosed subject matter. In some embodiments, the composition comprises a peptide comprising, consisting essentially of, or consisting of the amino acid sequence, RTVRCTCI (SEQ ID NO: 2), the amino acid sequence LSRTVRCTCISI (SEQ ID NO: 3), the amino acid sequence VPLSRTVRCTCISI (SEQ ID NO: 4), a modified peptide thereof, a fragment thereof, or a combination thereof.

Similarly, the presently disclosed subject matter also provides in some embodiments methods for inducing a subject's immune system against a pathogen by administering to the subject a composition comprising a peptide comprising, consisting essentially of, or consisting of the amino acid sequence, RTVRCTCI (SEQ ID NO: 2), the amino acid sequence LSRTVRCTCISI (SEQ ID NO: 3), the amino acid sequence VPLSRTVRCTCISI (SEQ ID NO: 4), a modified peptide thereof, a fragment thereof, or a combination thereof.

In some embodiments of the presently disclosed peptides, the N-terminal VP amino acids are required. In some embodiments, D-peptides are not expected to engage the immune system, e.g., not expected to activate the cellular receptor and induce immune-cell recruitment. See FIG. 12. Incidentally , D-peptides are also expected to be more stable—as they are less susceptible to protease degradation. In some embodiments, the peptides (either L-amino acid versions or D-amino acid versions) bind the receptor, but do not activate it. These act as inhibitors and can be employed to reduce inflammation. This is another application for CXCL10-derived peptides in accordance with the presently disclosed subject matter. Indeed, inhibition of the CXCL10-CXCR3 receptor signaling axis has been shown to be therapeutically beneficial in a number of disease states.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1 hCXCL10-derived Peptide Library Screens

The 77 amino acid mature human CXCL10 polypeptide (see amino acids 22-98 of Accession No. NP_001556.2 of the GENBANK® biosequence database) was divided into seven (7) overlapping peptides denoted P1-P6 and P8 (SEQ ID NOs: 4-10, respectively) and one larger C-terminal peptide denoted P9 (SEQ ID NO: 11), each of which were tested for bactericidal activity on CRE *K. pneumoniae* at 5.6 μM peptide concentration.

Figure 2:
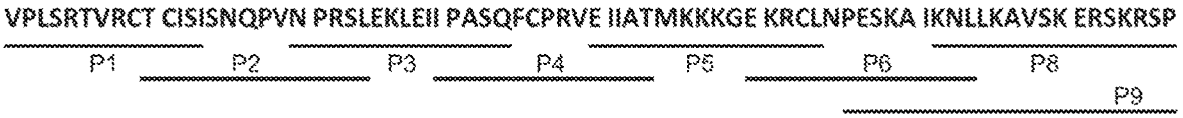
FIG. 2 is a depiction of the production of an initial hCXCL10-derived peptide library. Synthetic 14- to 22-mer overlapping peptides were generated from the primary amino acid sequence of mature human CXCL10 (shown at top; SEQ ID NO: 1). The amino acid sequences of Peptides P1-P6, P8, and P9 (SEQ ID NOs: 4-11, respectively) are shown. No Peptide P7 was synthesized.

FIG. 2 is a depiction of the production of an initial hCXCL10-derived peptide library. Synthetic 14- to 22-mer overlapping peptides were generated from the primary amino acid sequence of mature human CXCL10 (shown at top; SEQ ID NO: 1). The amino acid sequences of Peptide P1-Peptide P6, Peptide P8, and Peptide P9 (SEQ ID NOs: 4-11, respectively) are shown. No Peptide P7 was synthesized.

Figure 3:
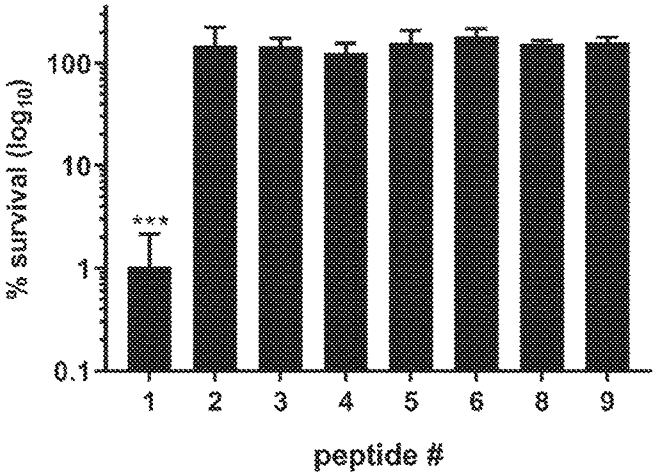
FIG. 3 is a bar graph showing the levels of bactericidal activities of hCXCL10-derived Peptides P1-P6, P8, and P9 (SEQ ID NOs: 4-11, respectively) against *B. anthracis* vegetative bacilli. *B. anthracis* Sterne strain 7702 bacilli ($2.5\times10^5$ cfu/ml) were treated with 22.4 μM of the indicated peptides for 2 hours at 37° C. in RPMI/HEPES prior to measuring viability via colony forming unit (cfu) determination. Data, expressed as percent survival relative to the untreated control (log 10), are shown as mean±standard error of the mean (SEM). Each Peptide was tested in triplicate. *** $p<0.001$ as compared to the untreated control.

FIG. 3 is a bar graph showing the levels of bactericidal activities of hCXCL10-derived Peptides P1-P6, P8, and P9 (SEQ ID NOs: 4-11, respectively) against *B. anthracis* vegetative bacilli. *B. anthracis* Sterne strain 7702 bacilli ($2.5\times10^5$ cfu/ml) were treated with 22.4 μM of the indicated peptides for 2 hours at 37° C. in RPMI/HEPES prior to measuring viability via colony forming unit (cfu) determination. Data, expressed as percent survival relative to the untreated control (log 10), are shown as mean±standard error of the mean (SEM). Each peptide was tested in triplicate. *** $p<0.001$ as compared to the untreated control.

Figure 4:
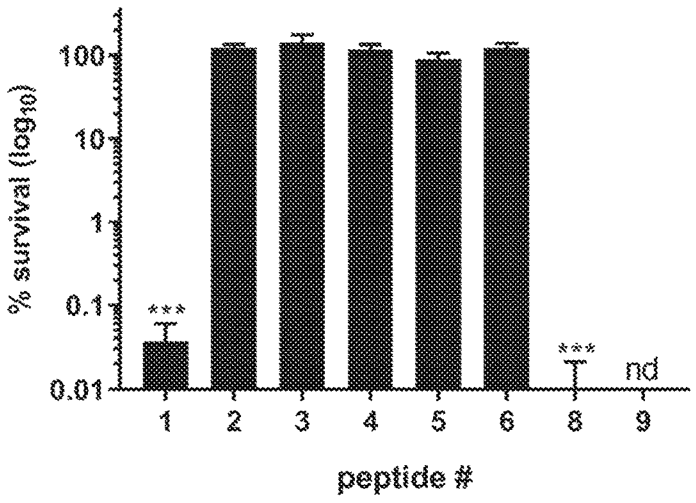
FIG. 4 is a bar graph showing the levels of bactericidal activities of hCXCL10-derived peptides against *K. pneumoniae*. CRE *K. pneumoniae* ($2.5\times10^5$ cfu/ml) were treated with 5.6 μM of the indicated peptides for 2 hours at 37° C. in 10 mM potassium phosphate buffer supplemented with 1% Tryptic Soy Broth prior to measuring viability via cfu determination. Data, expressed as percent survival relative to the untreated control (log 10), are the mean±SEM. n=3 per Peptide. *** $p<0.001$ as compared to the untreated control. nd=none detected (<50 cfu/ml).

FIG. 4 is a bar graph showing the levels of bactericidal activities of hCXCL10-derived peptides against *K. pneumoniae*. CRE *K. pneumoniae* ($2.5\times10^5$ cfu/ml) were treated with 5.6 µM of the indicated peptides for 2 hours at 37° C. in 10 mM potassium phosphate buffer supplemented with 1% Tryptic Soy Broth prior to measuring viability via cfu determination. Data, expressed as percent survival relative to the untreated control (log 10), are the mean±SEM. n=3 per peptide. *** $p<0.001$ as compared to the untreated control. nd=none detected (<50 cfu/ml).

Figure 5:
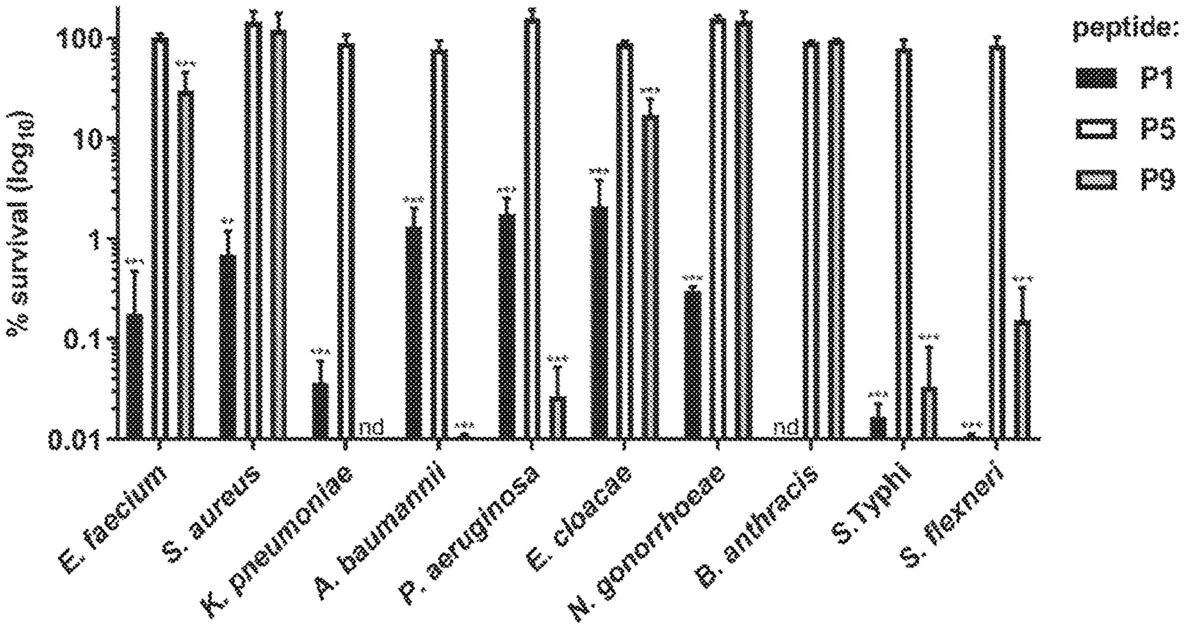
FIG. 5 is a bar graph showing broad-spectrum bactericidal activity of Peptides P1 (SEQ ID NO: 4) and P9 (SEQ ID NO: 11) against diverse bacterial species. Killing of the indicated organisms by exposure to 1.4 μM (MDR *A. baumannii*), 2.8 μM (MDR *S. flexneri* and MDR S. *Typhi*), 5.6 μM (CRE *K. pneumoniae* and MDR *P. aeruginosa*), 11.2 μM (MRSA and VRE), 16.8 μM (MDR *Enterobacter cloacae*), or 22.4 μM (*N. gonorrhoeae* and *B. anthracis*) Peptide P1 (SEQ ID NO: 4), Peptide P9 (SEQ ID NO: 11), or the negative control Peptide P5 (SEQ ID NO: 8). Bacteria ($2.5\times10^5$ cfu/ml) were treated with individual peptides for 2 hours in RPMI/HEPES (*N. gonorrhoeae* and *B. anthracis*) or 10 mM potassium phosphate buffer supplemented with 1% Tryptic Soy Broth (all other organisms) prior to measuring viability via cfu determination. Data, expressed as % survival relative to the species-matched untreated control (log 10), are the mean±SEM, n=3 per Peptide. As complete killing in most groups would preclude meaningful comparisons across bacterial species, tested peptide concentrations nearest those killing ~99.0-99.9% of bacteria are shown. Marginally higher peptide concentrations were sufficient for killing the inoculums entirely. * $p<0.001$ and  $p<0.01$ as compared to the respective, species-matched Peptide P5 (SEQ ID NO: 8) control; nd=none detected (<50 cfu/ml).

FIG. 5 is a bar graph showing broad-spectrum bactericidal activity of Peptides P1 (SEQ ID NO: 4) and P9 (SEQ ID NO: 11) against diverse bacterial species. Killing of the indicated organisms by exposure to 1.4 µM (MDR *A. baumannii*), 2.8 µM (MDR *S. flexneri* and MDR S. *Typhi*), 5.6 µM (CRE *K. pneumoniae* and MDR *P. aeruginosa*), 11.2 µM (MRSA and VRE), 16.8 µM (MDR *Enterobacter cloacae*), or 22.4 µM (*N. gonorrhoeae* and *B. anthracis*) Peptide P1 (SEQ ID NO: 4), Peptide P9 (SEQ ID NO: 11), or the negative control Peptide P5 (SEQ ID NO: 8). Bacteria ($2.5\times10^5$ cfu/ml) were treated with individual peptides for 2 hours in RPMI/HEPES (*N. gonorrhoeae* and *B. anthracis*) or 10 mM potassium phosphate buffer supplemented with 1% Tryptic Soy Broth (all other organisms) prior to measuring viability via cfu determination. Data, expressed as % survival relative to the species-matched untreated control (log 10), are the mean±SEM, n=3 per Peptide. As complete killing in most groups would preclude meaningful comparisons across bacterial species, tested peptide concentrations nearest those killing ~99.0-99.9% of bacteria are shown. Marginally higher peptide concentrations were sufficient for killing the inoculums entirely. * $p<0.001$ and  $p<0.01$ as compared to the respective, species-matched Peptide P5 (SEQ ID NO: 8) control; nd=none detected (<10 cfu/ml).

Example 2

Sequence Specificity of Peptide P1Versus MDR Bacterial Strains

To test the sequence specificity of Peptide P1 (SEQ ID NO: 4), a scrambled version of Peptide P1 (SEQ ID NO: 86) was prepared and tested against *K. pneumoniae* and *S. flexneri*. Survival of CRE *K. pneumoniae* and MDR *S. flexneri* following exposure to 2.8 µM Peptide P1 (SEQ ID NO: 4), Peptide P5 (SEQ ID NO: 8; negative control), or a scrambled Peptide P1 variant ($P1_{scram}$; CSVPTITCRVRLIS; SEQ ID NO: 86) was tested.

Figure 6:
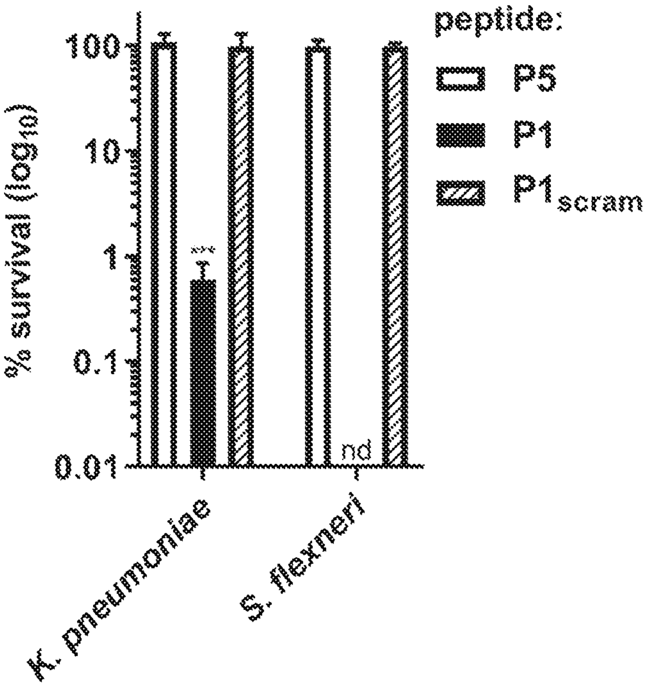
FIG. 6 is a bar graph showing that a scrambled Peptide P1 variant ($P1_{scram}$; SEQ ID NO: 86) did not kill bacteria. Survival of CRE *K. pneumoniae* and MDR *S. flexneri* following exposure to 2.8 μM Peptide P1 (SEQ ID NO: 4), Peptide P5 (SEQ ID NO: 8; negative control), or a scrambled Peptide P1 variant ($P1_{scram}$; CSVPTITCRVRLIS; SEQ ID NO: 86). Data, expressed as % survival relative to the untreated control (log 10), are the mean±SEM, n=3 per Peptide. *** $p<0.001$ as compared to the respective species-matched Peptide P5 (SEQ ID NO: 8) control; nd=none detected (<50 cfu/ml).

The results are presented in FIG. 6. The scrambled Peptide P1 variant ($P1_{scram}$; SEQ ID NO: 86) did not kill bacteria ($p<0.001$ as compared to the respective species-matched Peptide P5 (SEQ ID NO: 8)).

Example 3

Antibacterial Activities of Peptide P1, Modified Versions Thereof, and Conjugates Thereof Peptide P1 (SEQ ID NO: 4) was truncated at both the N-terminus and the C-terminus, and these truncated peptides along with a conjugate were tested for activity against CRE *K. pneumoniae*, MRSA, *A. baumannii*, and *S. typhi*. The truncations included removal of the first two amino acids to produce Peptide ΔVP (SEQ ID NO: 3) and then using Peptide ΔVP as a starting material, six additional C-terminal truncated peptides were constructed, each one with one amino acid removed from the C-terminus.

Figure 7:
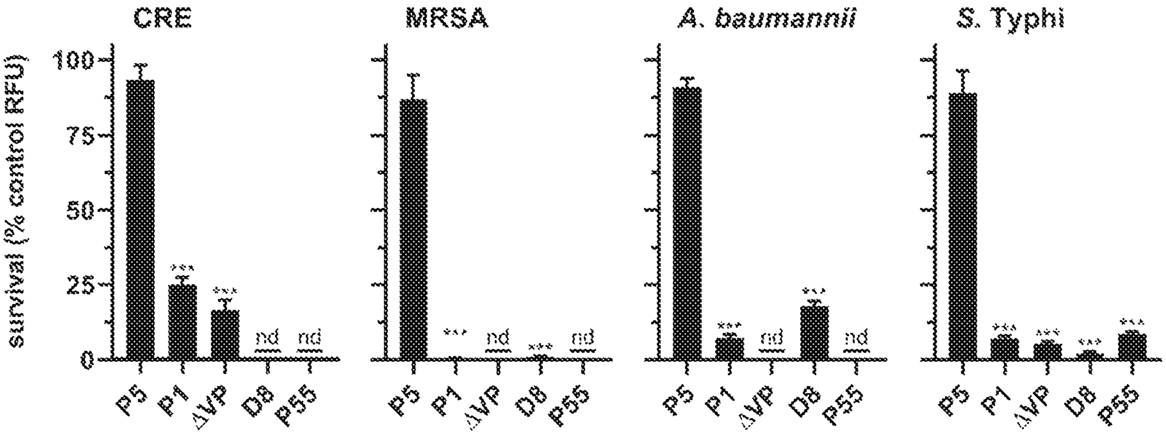
FIG. 7 is a series of bar graphs showing bactericidal activities of Peptides P1 (SEQ ID NO: 4), ΔVP (SEQ ID NO: 3), D8 (SEQ ID NO: 2, with all amino acids being D-amino acids), and P55 (SEQ ID NO: 13) against MDR bacterial pathogens. Microbial killing exhibited by 50 μM Peptide P1 (SEQ ID NO: 4), the truncated Peptide P1 variant ΔVP (SEQ ID NO: 3), the all D-amino acid 8-mer Peptide D8 (SEQ ID NO: 2), and the P1-GGG-P9 conjugate Peptide P55 (SEQ ID NO: 13) against $2.5\times10^5$ cfu/ml of CRE *K. pneumoniae*, MRSA, MDR *A. baumannii*, or MDR *S. Typhi* in RPMI/HEPES. The survival of each organism following exposure to the negative control Peptide P5 (SEQ ID NO: 8) is also shown. Bacterial viability was determined using the fluorescent viability reagent ALAMARBLUE™ (Thermo Fisher Scientific Inc., Waltham, Massachusetts, United States of America). Data are expressed as relative fluorescence units (RFU; determined following normalization to untreated samples included in each experiment for each organism) and represent the mean±SEM, n=3 per Peptide. *** $p<0.001$ as compared to the respective species-matched Peptide P5 (SEQ ID NO: 8) control; nd=none detected (<50 cfu/ml).

FIG. 7 is a series of bar graphs showing bactericidal activities of Peptides P1 (SEQ ID NO: 4), ΔVP (SEQ ID NO: 3), D8 (SEQ ID NO: 2), with all amino acids being D-amino acids), and conjugate P55 (SEQ ID NO: 13) against MDR bacterial pathogens. Microbial killing exhibited by 50 µM Peptide P1 (SEQ ID NO: 4), the truncated Peptide P1 variant ΔVP (SEQ ID NO: 3), the all D-amino acid 8-mer Peptide D8 (SEQ ID NO: 2), and the P1-GGG-P9 conjugate Peptide P55 (SEQ ID NO: 13) against $2.5\times10^5$ cfu/ml of CRE *K. pneumoniae*, MRSA, MDR *A. baumannii*, or MDR S. *Typhi* in RPMI/HEPES. The survival of each organism following exposure to the negative control Peptide P5 (SEQ ID NO: 8) is also shown. Bacterial viability was determined using the fluorescent viability reagent ALAMARBLUE™ (Thermo Fisher Scientific Inc., Waltham, Massachusetts, United States of America). In each case, there were statistically significant differences between the bactericidal activities of Peptides P1 (SEQ ID NO: 4), ΔVP (SEQ ID NO: 3), D8 (SEQ ID NO: 2), with all amino acids being D-amino acids), and conjugate P55 (SEQ ID NO: 13) versus control Peptide P5 (SEQ ID NO: 8).

Figure 8:
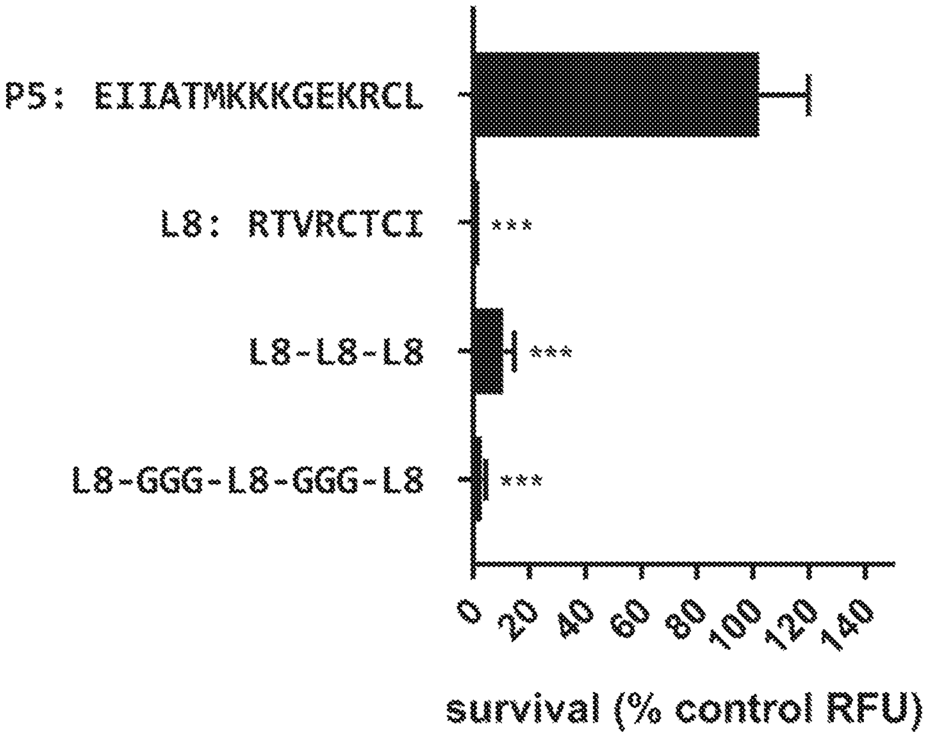
FIG. 8 is a bar graph showing bactericidal activities of linear polymers composed of Peptide L8 (SEQ ID NO: 2, with all amino acids being L-amino acids). Killing of CRE *K. pneumoniae* following exposure to 50 μM Peptide L8 (SEQ ID NO: 2) or linear polymers of this peptide without (SEQ ID NO: 92) and with (SEQ ID NO: 93) tri-glycine linkers (GGG). The negative control Peptide P5 (SEQ ID NO: 8) is also shown. Bacteria ($2.5\times10^5$ cfu/ml) were treated with individual peptides or polymers for 2 hours in RPMI/HEPES prior to measuring bacterial viability using ALAMARBLUE™ (Thermo Fisher Scientific Inc.). Data, expressed as RFU determined following normalization to untreated samples, are the mean±SEM, n=4 per Peptide. *** $p<0.001$ as compared to the Peptide P5 (SEQ ID NO: 8) control.

FIG. 8 is a bar graph showing bactericidal activities of linear polymers composed of Peptide L8 (SEQ ID NO: 2, with all amino acids being L-amino acids). Killing of CRE *K. pneumoniae* following exposure to 50 µM Peptide L8 (SEQ ID NO: 2) or linear trimers of this peptide without (L8-L8-L8; SEQ ID NO: 87) and with (L8-GGG-L8-GGG-L8; SEQ ID NO: 87) tri-glycine linkers. The negative control Peptide P5 (SEQ ID NO: 8) is also shown. Bacteria ($2.5\times10^5$ cfu/ml) were treated with individual peptides or trimers for 2 hours in RPMI/HEPES prior to measuring bacterial viability using ALAMARBLUE™ (Thermo Fisher Scientific Inc.). L8 (SEQ ID NO: 2) L8-L8-L8 (SEQ ID NO: 87) and L8-GGG-L8-GGG-L8 (SEQ ID NO: 87) all killed CRE *K. pneumoniae* statistically significantly more effectively than Peptide P5 (SEQ ID NO: 8).

Figure 9:
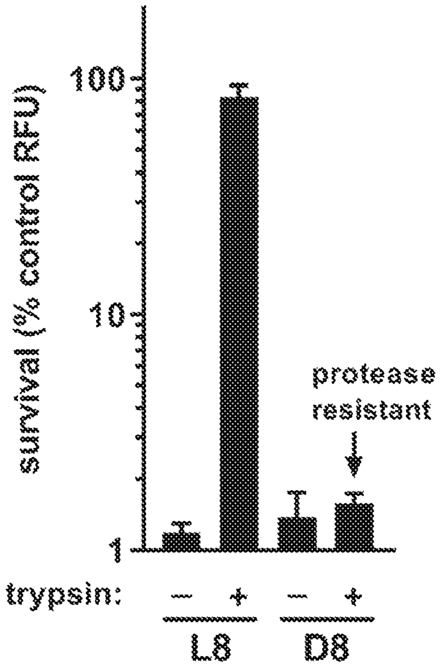
FIG. 9 is a bar graph showing the resistance of Peptide D8 (SEQ ID NO: 2, with all amino acids being D-amino acids) to proteolytic degradation. Killing of CRE *K. pneumoniae* by 50 μM Peptide D8 (SEQ ID NO: 2) or the all L-amino acid version of this peptide (Peptide L8; SEQ ID NO: 2) pretreated±trypsin protease (200:1 molar ratio) for 2 hours in 50 mM Tris-HCl buffer supplemented with 20 mM $CaCl_2$). Data, expressed as RFU determined following normalization to untreated samples, are the mean±SEM, n=3 per Peptide. Peptide D8 (SEQ ID NO: 2) was resistant to proteolytic degradation, retaining antimicrobial activity after incubation with trypsin (arrow).

An all D-amino acid version of Peptide L8 (Peptide D8; SEQ ID NO: 2) was produced and tested for activity against CRE *K. pneumoniae*. Killing of CRE *K. pneumoniae* by 50 µM Peptide D8 (SEQ ID NO: 2) or the all L-amino acid version of this peptide (Peptide L8; SEQ ID NO: 2) pre-treated+trypsin protease (200:1 molar ratio) for 2 hours in 50 mM Tris-HCl buffer supplemented with 20 mM $CaCl_2$) was tested/The results are presented in FIG. 9. Peptide D8 (SEQ ID NO: 2, with all amino acids being D-amino acids) was resistant to proteolytic degradation activity after incubation with trypsin (arrow), whereas Peptide L8 (SEQ ID NO: 2, with all amino acids being L-amino acids) was not.

CRE *K. pneumoniae* ($2.5\times10^5$ cfu/ml) were treated with the indicated concentrations of Peptides P1 (SEQ ID NO: 4), P9 (SEQ ID NO: 11), or P1 (SEQ ID NO: 2)+P9 (SEQ ID NO: 11) together (SEQ ID NO: 94), the conjugate Peptides P55 (SEQ ID NO: 13) or P59 (SEQ ID NO: 14), or the negative control Peptide P5 (SEQ ID NO: 8) in 10 mM potassium phosphate buffer supplemented with 1% Tryptic Soy Broth (left graph) or RPMI/HEPES (right graph) for 2 hours at 37° C. prior to measuring bacterial viability using ALAMARBLUE™ (Thermo Fisher Scientific Inc.).

Figure 10:
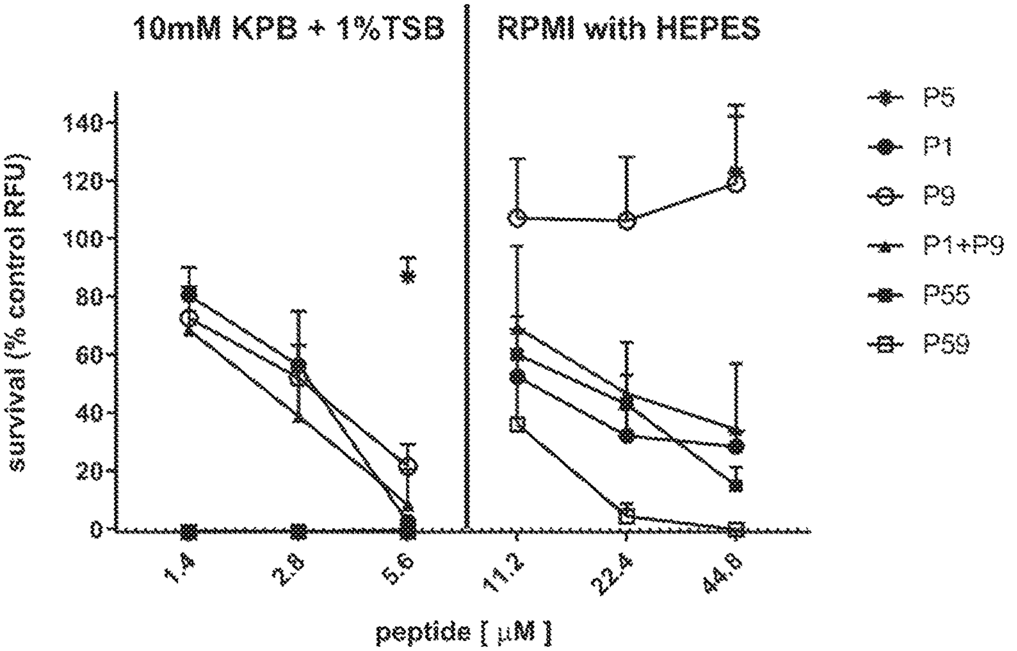
FIG. 10 is a pair of bar graphs showing bactericidal activities of the listed conjugate peptides in hypotonic versus physiologic medium. CRE *K. pneumoniae* ($2.5\times10^5$ cfu/ml) were treated with the indicated concentrations of Peptides P1 (SEQ ID NO: 4), P9 (SEQ ID NO: 11), or P1 (SEQ ID NO: 2)+P9 (SEQ ID NO: 11) together (SEQ ID NO: 94), the conjugate Peptides P55 (SEQ ID NO: 13) or P59 (SEQ ID NO: 14), or the negative control Peptide P5 (SEQ ID NO: 8) in 10 mM potassium phosphate buffer supplemented with 1% Tryptic Soy Broth (left graph) or RPMI/HEPES (right graph) for 2 hours at 37° C. prior to measuring bacterial viability using ALAMARBLUE™ (Thermo Fisher Scientific Inc.). Data, expressed as RFU determined following normalization to untreated samples, are the mean±SEM, n=3 Per Peptide.

The results are presented in FIG. 10. Peptide P1 retained activity in RPMI (normosaline) but experienced solubility issues at higher concentrations. Peptide P9 lost activity in RPMI, but had activity in hypotonic buffer (10 mM KPB/1% TSB). Furthermore, both of the conjugate peptides were more effective than just Peptide P1 and Peptide P9 individually or when Peptide P1 and Peptide P9 were added together to the same well. Both conjugate peptides also retained activity in RPMI, and no solubility issues have been noted to date.

Figure 11:
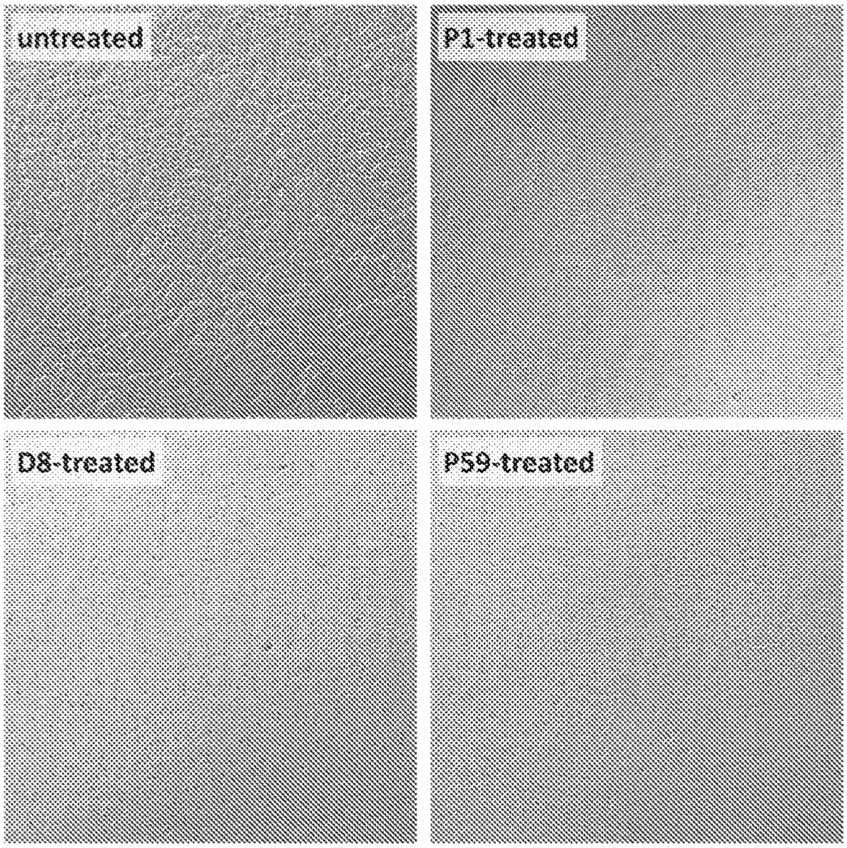
FIG. 11 is a series of photomicrographs showing peptide-mediated antimicrobial effects against *B. anthracis* spores. *B. anthracis* Sterne strain 7702 spores ($1.0\times10^7$ cfu/ml) were treated with 50 μM of Peptide P1 (SEQ ID NO: 4), D8 (SEQ ID NO: 2), or P59 (SEQ ID NO: 14) in RPMI/HEPES+2% fetal bovine serum (FBS). Untreated spores were also assayed. Spore germination and vegetative outgrowth were monitored using light microscopy. Representative fields from 3 independent experiments are shown at 200× magnification following 3 hours of treatment. Untreated spores underwent germination/outgrowth and are visualized as bacilli. In contrast, Peptides P1 (SEQ ID NO: 4), D8 (SEQ ID NO: 2), and P59 (SEQ ID NO: 14) each decreased spore germination as judged by markedly reduced numbers of bacilli 3 hours post-treatment.

*B. anthracis* Sterne strain 7702 spores ($1.0\times10^7$ cfu/ml) were treated with 50 μM of Peptide P1 (SEQ ID NO: 4), Peptide D8 (SEQ ID NO: 2), or Peptide P59 (SEQ ID NO: 14) in RPMI/HEPES+2% fetal bovine serum (FBS). Untreated spores were also assayed. Spore germination and vegetative outgrowth were monitored using light microscopy. The results are presented in FIG. 11, which is a series of photomicrographs showing peptide-mediated antimicrobial effects against *B. anthracis* spores. Representative fields from 3 independent experiments are shown at 200× magnification following 3 hours of treatment. Untreated spores underwent germination/outgrowth and are visualized as bacilli. In contrast, Peptide P1 (SEQ ID NO: 4), Peptide D8 (SEQ ID NO: 2), and Peptide P59 (SEQ ID NO: 14) each reduced spore germination as judged by markedly reduced numbers of bacilli three hours post-treatment.

Example 4

Host-Targeted Bioregulatory Activities of hCXCL10-Derived Peptides

Figure 12A:
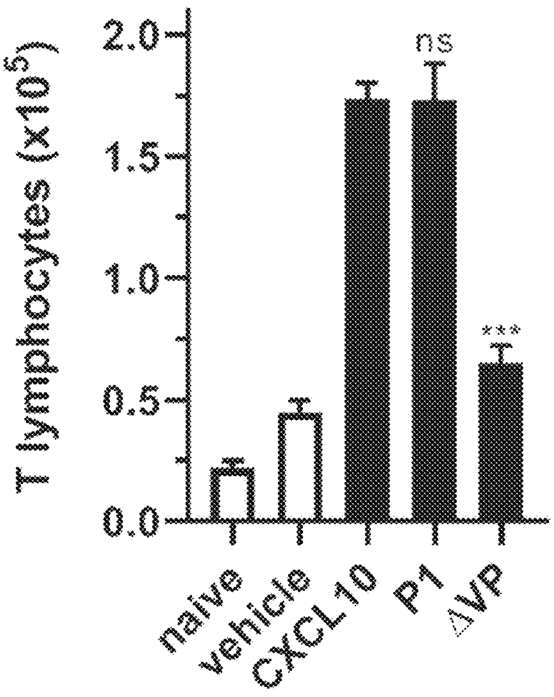
FIGS. 12A and 12B are bar graphs showing host-targeted bioregulatory effects of hCXCL10-derived peptides.
Figure 12B:
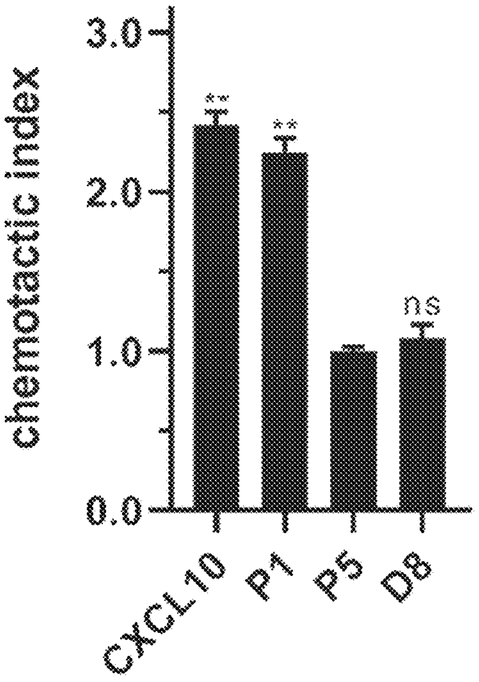

FIGS. 12A and 12B are bar graphs showing host-targeted bioregulatory effects of hCXCL10-derived peptides. FIG. 12A is a bar graph showing in vivo recruitment/infiltration of CD45+/CD3+T lymphocytes was measured in peritoneal lavages collected 6 hours after intraperitoneal injection of saline alone or equimolar amounts of recombinant human CXCL10 (SEQ ID NO: 1; Peptide P1 (SEQ ID NO: 4), or peptide ΔVP (SEQ ID NO: 3) into C57BL/6 mice. T-cell counts from naïve animals are shown as a baseline control of immune-cell localization. Cellular infiltrates were quantified using flow cytometry. Data, expressed as absolute cell number, are the mean±SEM, n=4 male+4 female animal per group. FIG. 12B is a bar graph showing in vitro human T-cell migration in response to 25 nM hCXCL10 (SEQ ID NO: 1), or Peptide P5 (SEQ ID NO: 8), Peptide P1 (SEQ ID NO: 4), or Peptide D8 (SEQ ID NO: 2) was measured using the CHEMOTX® trans-well system (Neuro Probe, Inc., Gaithersburg, Maryland, United States of America).

Example 5

Toxicity of hCXCL10-Derived Peptides as Measured by Hemolysis

Figure 13:
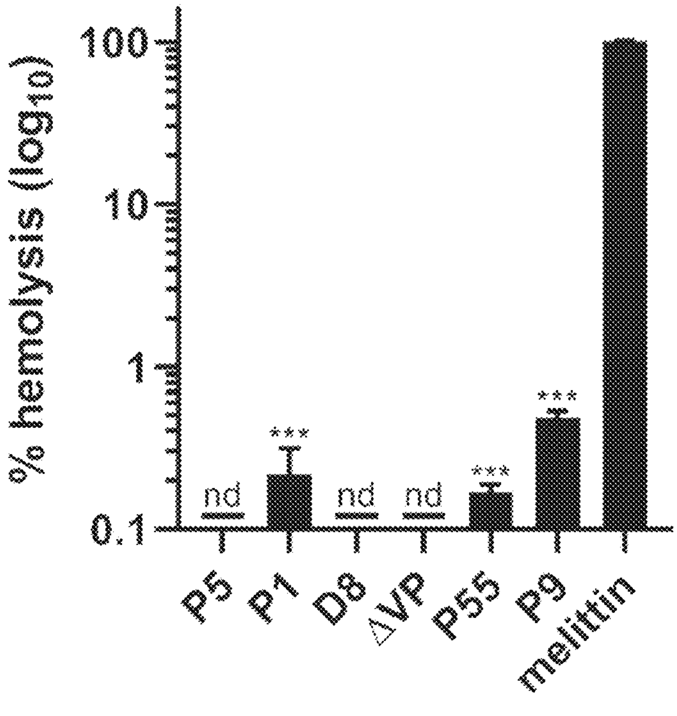
FIG. 13 is a bar graph showing cytotoxicity screening of antimicrobial peptides P55 (SEQ ID NO: 13) and P9 (SEQ ID NO: 11). Hemolysis of human red blood cells, as measured using spectrometry (540 nm), after 1 hour of exposure to 80 μM of the indicated peptide or 8 μM of the cytolytic peptide melittin (positive control). All hCXCL10-derived peptides resulted in less than 1% hemolysis. n=3 per Peptide. *** $p<0.001$ as compared to melittin; nd=none detected (<0.1% hemolysis).

Hemolysis of human red blood cells, as measured using spectrometry (540 nm), after 1 hour of exposure to 80 μM of the indicated peptide or 8 μM of the cytolytic peptide melittin (positive control). The results are presented in FIG. 13. All hCXCL10-derived peptides resulted in less than 1% hemolysis. n=3. *** $p<0.001$ as compared to melittin; nd=none detected (<0.1% hemolysis).

Example 5

In Vivo Antibacterial Activity

The ability to prevent/cure wound infections caused by *K. pneumoniae* was tested. Full-thickness wounds were generated in C57BL/6 mice and inoculated with an $LD_{50}$ ($1\times10^3$ cfu total) of *K. pneumoniae* ATCC 43816. Infected wounds were treated with 10 μl of 1.2% Peptide D8 (SEQ ID NO: 2) prepared in saline, or an equivalent volume of saline alone, 4 hours post-infection and then twice per day for 4 days.

Figure 14C:
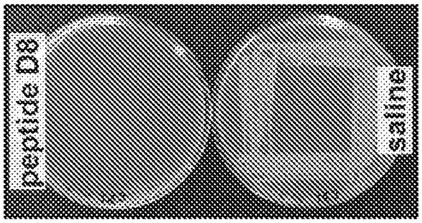
FIGS. 14A-14C presents the results of experiments showing that Peptide D8 (SEQ ID NO: 2) prevented/cured wound infections caused by *K. pneumoniae*. Full-thickness wounds were generated in C57BL/6 mice and inoculated with an $LD_{50}$ ($1\times10^3$ cfu total) of *K. pneumoniae* ATCC 43816. Infected wounds were treated with 10 μl of 1.2% Peptide D8 (SEQ ID NO: 2) prepared in saline, or an equivalent volume of saline alone, 4 hours post-infection and then twice per day for 4 days.
Figure 14B:
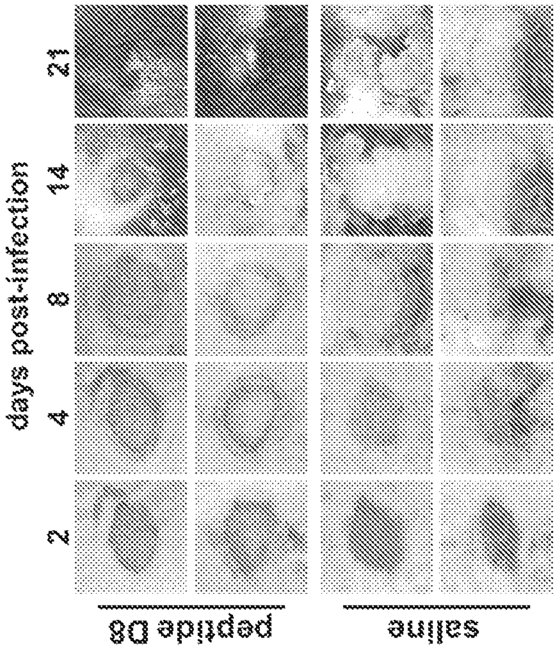
Figure 14A:
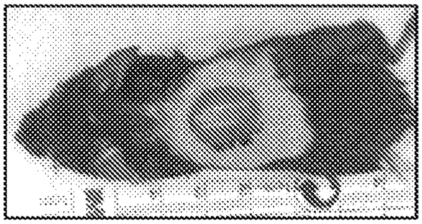
Figure 14A:
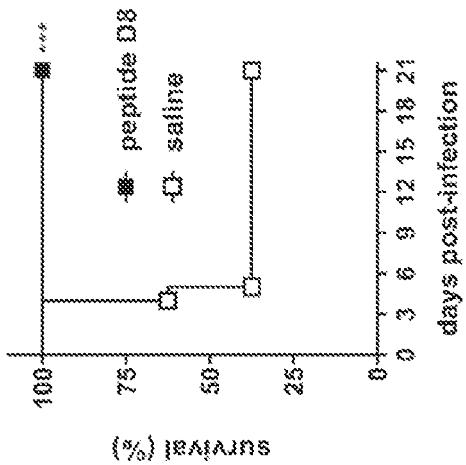
Figure 15:
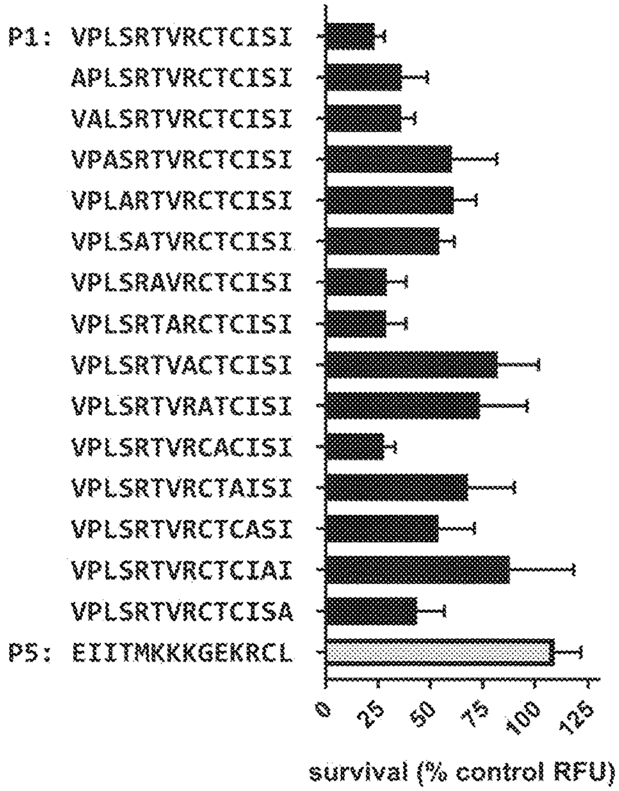
FIG. 15 is a bar graph showing bactericidal activities of Peptide P1 alanine scan variants (SEQ ID NOs: 4 and 33-46) against CRE *K. pneumoniae*. CRE *K. pneumoniae* ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.
Figure 16:
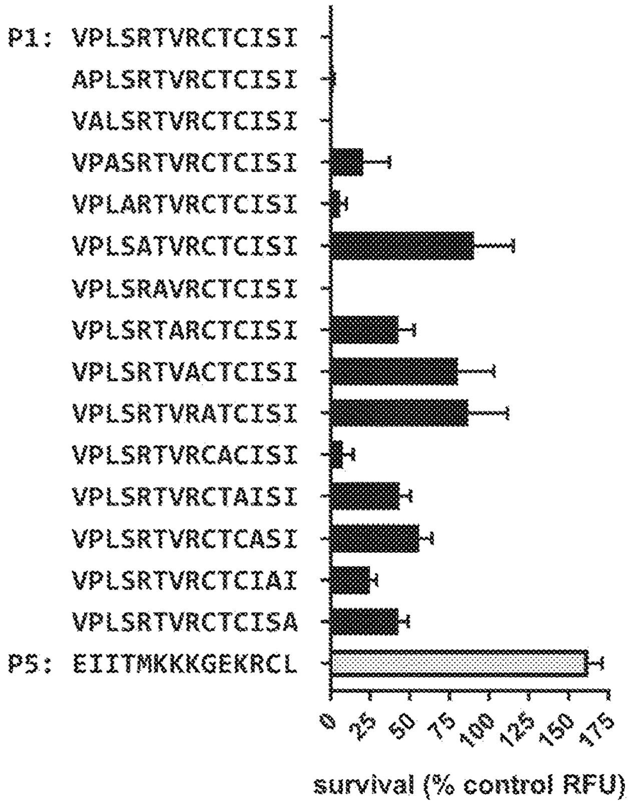
FIG. 16 is a bar graph showing bactericidal activities of Peptide P1 alanine scan variants (SEQ ID NOs: 4 and 33-46) against MRSA. MRSA ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.
Figure 17:
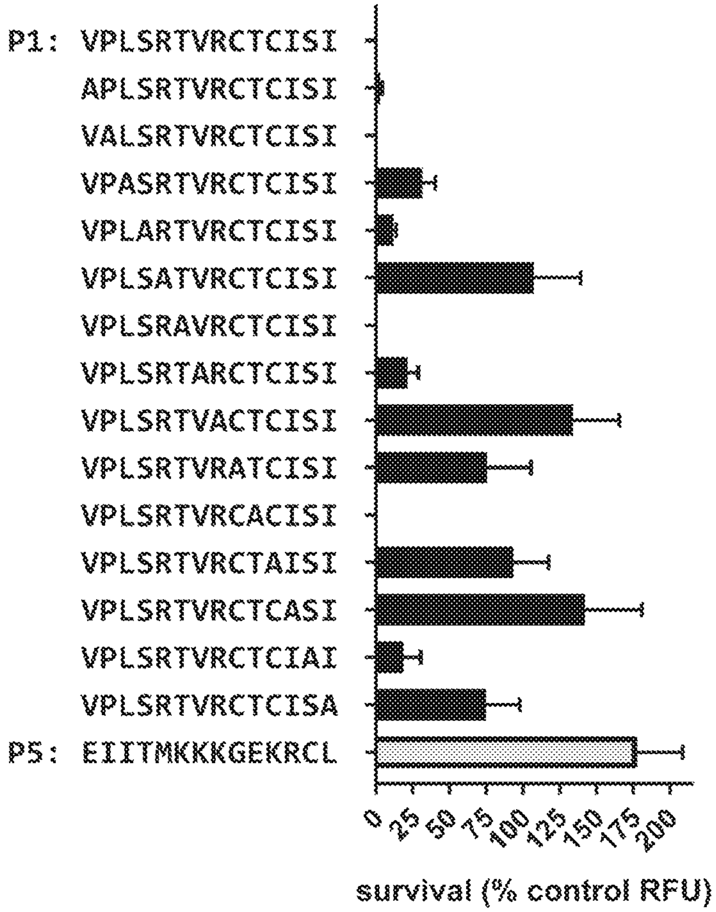
FIG. 17 is a bar graph showing bactericidal activities of Peptide P1 alanine scan variants (SEQ ID NOs: 4 and 33-46) against MDR *A. baumannii*. MDR *A. baumannii* ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. Data, expressed as RFU determined following normalization to untreated samples, are the mean±SEM, n=3 per Peptide.

The results are presented in FIGS. 14A-14C. FIG. 14A is a graph showing mortality among infected peptide- and saline-treated animals. Kaplan-Meier survival curves represent the combined mortality from 8 mice total per group. Treatment with Peptide D8 (SEQ ID NO: 2) resulted in a statistically significant increase in survival (*** $p<0.001$ as compared to saline controls).

Wound status over the course of infection was also observed as shown in FIG. 14B. Representative image sets from pairs of peptide- and saline-treated animals surviving through day 21 are shown. In peptide-treated wounds, bacterial infection was resolved and healing occurred. In contrast, the infected wounds of saline-treated mice deteriorated significantly, remaining heavily infected and unhealed at the end of observation.

Wound swabs were streaked onto lysogeny broth (LB) agar to assess bacterial burden at day 14 post-infection (see FIG. 14C). No bacterial growth was observed for swabs taken from peptide-treated wounds; heavy growth was observed for those taken from saline-treated wounds.

Example 6

Alanine Scanning of Peptide P1 and Peptide P9 Against MDR Bacteria

Bactericidal activities of Peptide P1 alanine scan variants (SEQ ID NOs: 4 and 33-46) against CRE *K. pneumoniae* were tested. CRE *K. pneumoniae* ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 15.

Bactericidal activities of Peptide P1 alanine scan variants (SEQ ID NOs: 4 and 33-46) against MRSA were also tested. MRSA ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 16.

Bactericidal activities of Peptide P1 alanine scan variants (SEQ ID NOs: 4 and 33-46) against MDR *A. baumannii* were also tested. MDR *A. baumannii* ($2.5\times10^5$ cfu/ml) were treated with 50 μM of the indicated Peptide P1 alanine scan variants (SEQ ID NOs: 4 and 33-46) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 17.

Bactericidal activities of Peptide P9 alanine scan variants (SEQ ID NOs: 11 and 47-66) against CRE *K. pneumoniae* were also tested. CRE *K. pneumoniae* ($2.5\times10^5$ cfu/ml) were treated with 5.6 μM of the indicated Peptide P9 alanine scan variants (SEQ ID NOs: 11 and 47-66) in 10 mM potassium phosphate buffer supplemented with 1% Tryptic Soy Broth for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 18.

Example 7

Bactericidal Activities of Peptide P9 Modifications Against CRE *K. pneumoniae*

Figure 19:
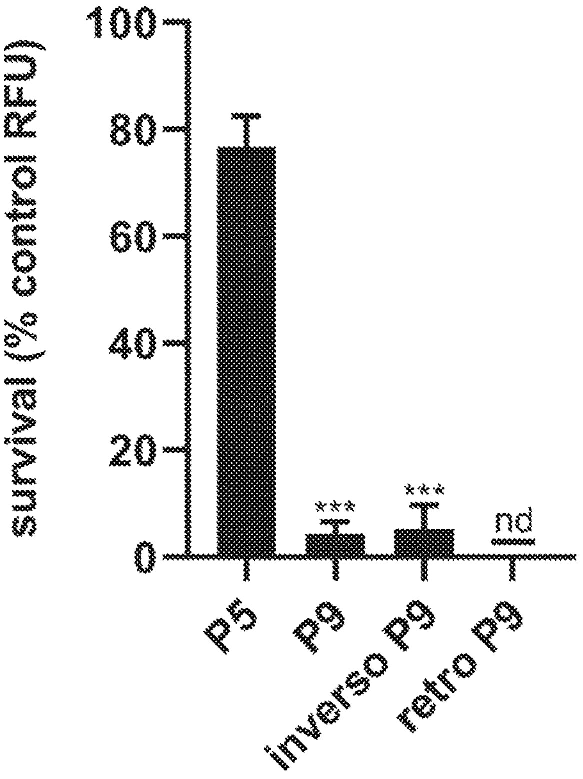
FIG. 19 is a bar graph showing bactericidal activities of Peptide P9 inverso (SEQ ID NO: 11) and retro (SEQ ID NO: 91) variants. Killing of CRE *K. pneumoniae* by 5.6 μM Peptide P9 (SEQ ID NO: 11), an all D-amino acid variant (inverso), an L-amino acid variant in which the Peptide P9 amino acid sequence (SEQ ID NO: 91) is in the reverse order (retro), and the negative control Peptide P5 (SEQ ID NO: 8) in 10 mM potassium phosphate buffer supplemented with 1% Tryptic Soy Broth. Data, expressed as RFU determined following normalization to untreated samples, are the mean±SEM, n=3 per Peptide.

Bactericidal activities of Peptide P9 inverso (SEQ ID NO: 11) and retro (SEQ ID NO: 91) variants were tested. Killing of CRE *K. pneumoniae* by 5.6 μM Peptide P9 (SEQ ID NO: 11), an all D-amino acid variant (inverso), an L-amino acid variant in which the Peptide P9 amino acid sequence (SEQ ID NO: 91) is in the reverse order (retro), and the negative control Peptide P5 (SEQ ID NO: 8) in 10 mM potassium phosphate buffer supplemented with 1% Tryptic Soy Broth. The results are presented in FIG. 19.

Bactericidal activities of unstapled and stapled Peptide P9 variants (SEQ ID NO: 89) were also tested. CRE *K. pneumoniae* ($2.5\times10^5$ cfu/ml) were treated with 50 μM Peptide P9 (SEQ ID NO: 11), an unstapled variant containing 2-(4-pentenyl) alanine (pA; SEQ ID NO: 89), or a stapled variant (SEQ ID NO: 89) in which the alkene groups of the pA residues were coupled in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 20.

Example 8

Bactericidal Activities of Peptides L8 and D8 and Modified Variants Thereof Against CRE *K. pneumoniae*

Bactericidal activities of Peptide L8 alanine scan variants (SEQ ID NOs: 2 and 25-32) against CRE *K. pneumoniae* were tested. CRE *K. pneumoniae* ($2.5\times10^5$ cfu/ml) were treated with 50 μM of the indicated Peptide L8 alanine scan variants (SEQ ID NOs: 2 and 25-32) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) is also presented. The results are presented in FIG. 21/

Bactericidal activities of Peptide D8 D-alanine scan variants (SEQ ID NOs: 2 and 25-32) against CRE *K. pneumoniae* were also tested. CRE *K. pneumoniae* ($2.5\times10^5$ cfu/ml) were treated with 50 μM of the indicated Peptide D8 D-alanine scan variants (SEQ ID NOs: 2 and 25-32) in RPMI/HEPES for 2 hours at 37° C. prior to measuring bacterial viability using ALAMARBLUE™ (Thermo Fisher Scientific Inc.). Survival following exposure to the negative control Peptide P5 (SEQ ID NO: 8) was also tested. The results are presented in FIG. 21.

Bactericidal activities of Peptide D8, position 2 substitution variants (SEQ ID NOs: 2 and 67-85) against CRE *K. pneumoniae* were also tested. CRE *K. pneumoniae* ($2.5\times10^5$ cfu/ml) were treated with 50 μM of Peptide D8 (SEQ ID NO: 2) or Peptide D8 amino acid position 2 substitution variants (SEQ ID NOs: 67-85) in which the threonine at position 2 of Peptide D8 (SEQ ID NO: 2) was substituted with other D-amino acids. Bacterial survival was assessed in RPMI/HEPES using ALAMARBLUE™ (Thermo Fisher Scientific Inc.). Survival following exposure to the negative control Peptide P5 (SEQ ID NO: 8) was also tested. The results are presented in FIG. 23.

Example 9

Exemplary Therapies for Combating Bacterial Infections

Figure 24:
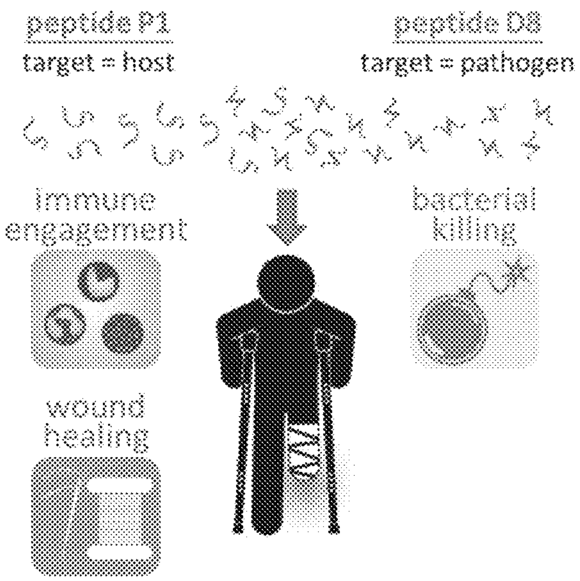
FIG. 24 is a schematic representation of multi-fold therapy for combating wound/surgical site infections. hCXCL10-derived peptides (e.g., Peptide P1 (SEQ ID NO: 4) or Peptide D8 (SEQ ID NO: 2) are administered topically, directly into the wound bed, to prevent/cure wound infections caused by MDR bacteria. Peptides alone, or in combination, directly kill the bacteria and recruit host immune cells to the site of infection according to the tailored degree of bioregulatory activity possessed by the particular peptide(s). Additionally, as hCXCL10 also promotes wound healing, it is expected peptides that exhibit host-targeted effects also accelerate tissue repair/regeneration.

FIG. 24 is a schematic representation of multi-fold therapy for combating wound/surgical site infections. hCXCL10-derived peptides are administered topically, directly into the wound bed, to prevent/cure wound infections caused by MDR bacteria. Peptides alone, or in combination, directly kill the bacteria and recruit host immune cells to the site of infection according to the tailored degree of bioregulatory activity possessed by the particular peptide(s). Additionally, as hCXCL10 also promotes wound healing, it is expected peptides that exhibit host-targeted effects also accelerate tissue repair/regeneration.

Figure 25:
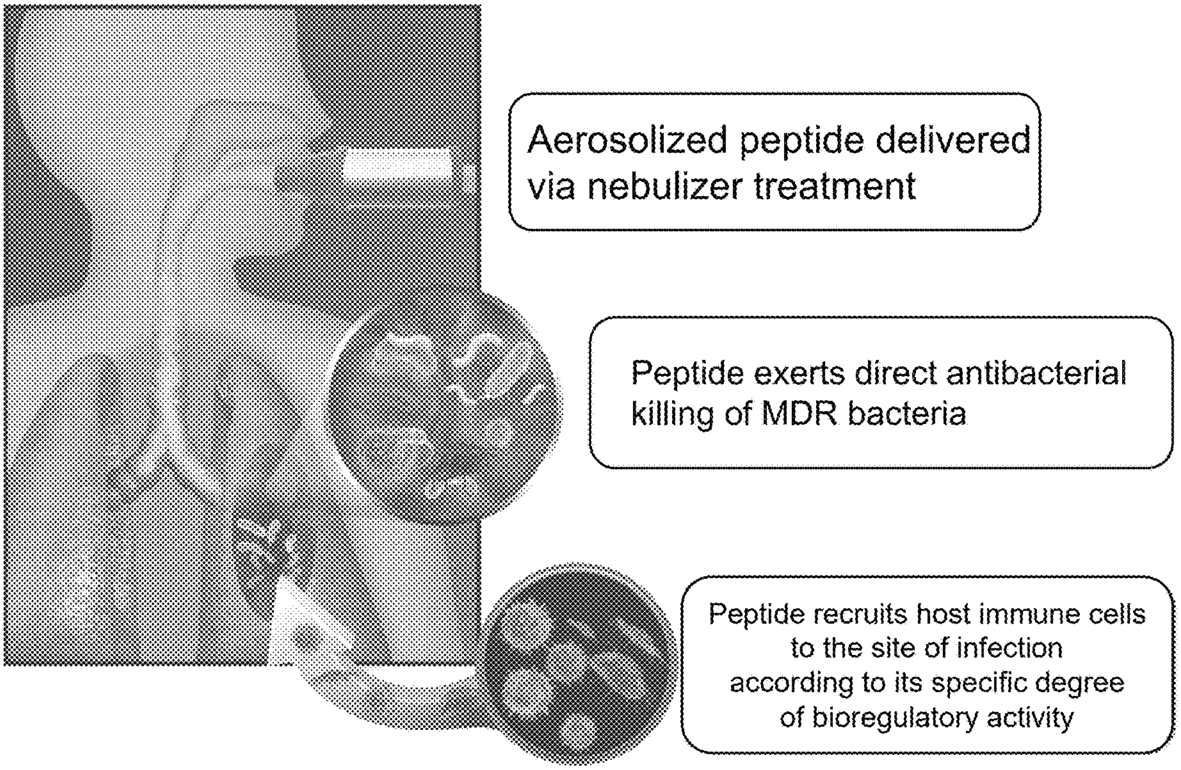
FIG. 25 is a schematic representation of aerosolized-peptide therapy to treat pulmonary infection. hCXCL10-derived peptides are administered to the lungs via nebulizer for the treatment of MDR bacterial pneumonia and/or inhalational biothreat exposure. Peptides alone, or in combination, directly kill the bacteria and recruit host immune cells to the site of infection according to the tailored degree of bioregulatory activity possessed by the particular peptide(s).

FIG. 25 is a schematic representation of aerosolized-peptide therapy to treat pulmonary infection. hCXCL10-derived peptides are administered to the lungs via nebulizer for the treatment of MDR bacterial pneumonia and/or inhalational biothreat exposure. Peptides alone, or in combination, directly kill the bacteria and recruit host immune cells to the site of infection according to the tailored degree of bioregulatory activity possessed by the particular peptide(s).

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A peptide consisting of RTVRCTCI (SEQ ID NO: 2), wherein each amino acid of SEQ ID NO: 2 is a D-amino acid.

2. The peptide of claim 1, wherein the peptide has bactericidal activity, bacteriostatic activity, or both against a bacterium selected from the group consisting of *Klebsiella pneumoniae* and *Bacillus anthracis.*

3. The peptide of claim 2, wherein the bacterium is a multi-drug resistant (MDR) strain of *K. pneumoniae.*

4. A pharmaceutical composition comprising the peptide of claim 1 and a pharmaceutically acceptable carrier, diluent, or excipient.

5. The pharmaceutical composition of claim 4, wherein the pharmaceutical composition is acceptable for administration to a human.

6. A composition comprising the peptide of claim 1, wherein the composition is formulated for a nebulizer, formulated for topical administration, or formulated for systemic administration.

7. A composition comprising the peptide of claim 1, wherein the peptide is polymer-functionalized, encapsulated in a particle, embedded in a solid support, embedded on a solid support, embedded in and on a solid support, or impregnated in a dressing, individually or in any combination thereof.

8. The composition of claim 7, wherein the peptide is formulated for release from the solid support or formulated for release from the dressing.

9. A medical device comprising a support layer with an antibacterial agent embedded therein or associated therewith, wherein the antibacterial agent comprises the peptide of claim 1.

10. The medical device of claim 9, wherein the peptide is encapsulated in a particle that is embedded in or associated with the support layer.

11. The medical device of claim 9, wherein the medical device is a wound dressing.

12. A method for inhibiting the growth of a bacterium, killing a bacterium, or both, the method comprising contacting the bacterium with an effective amount of a peptide of claim 1, wherein the bacterium is a *B. anthracis* bacterium or a *K. pneumoniae* bacterium.

13. The method of claim 12, wherein the *B. anthracis* bacterium comprises vegetative form, spore form, or both.

* * * * *

SEQUENCE LISTING

```
<160> NUMBER OF SEQ ID NOS: 94

<210> SEQ ID NO 1
<211> LENGTH: 77
<212> TYPE: PRT
<213> ORGANISM: Homo sapiens

<400> SEQUENCE: 1

Val Pro Leu Ser Arg Thr Val Arg Cys Thr Cys Ile Ser Ile Ser Asn
```

-continued 1 5 10 15

Gln Pro Val Asn Pro Arg Ser Leu Glu Lys Leu Glu Ile Ile Pro Ala
20 25 30

Ser Gln Phe Cys Pro Arg Val Glu Ile Ile Ala Thr Met Lys Lys Lys
35 40 45

Gly Glu Lys Arg Cys Leu Asn Pro Glu Ser Lys Ala Ile Lys Asn Leu
50 55 60

Leu Lys Ala Val Ser Lys Glu Arg Ser Lys Arg Ser Pro
65 70 75

<210> SEQ ID NO 2
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 2

Arg Thr Val Arg Cys Thr Cys Ile
1 5

<210> SEQ ID NO 3
<211> LENGTH: 12
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 3

Leu Ser Arg Thr Val Arg Cys Thr Cys Ile Ser Ile
1 5 10

<210> SEQ ID NO 4
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 4

Val Pro Leu Ser Arg Thr Val Arg Cys Thr Cys Ile Ser Ile
1 5 10

<210> SEQ ID NO 5
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 5

Thr Cys Ile Ser Ile Ser Asn Gln Pro Val Asn Pro Arg Ser Leu
1 5 10 15

<210> SEQ ID NO 6
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 6

```
Asn Pro Arg Ser Leu Glu Lys Leu Glu Ile Ile Pro Ala Ser Gln
1               5                   10                  15
```

<210> SEQ ID NO 7
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 7

```
Ile Pro Ala Ser Gln Phe Cys Pro Arg Val Glu Ile Ile Ala Thr
1               5                   10                  15
```

<210> SEQ ID NO 8
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 8

```
Glu Ile Ile Ala Thr Met Lys Lys Lys Gly Glu Lys Arg Cys Leu
1               5                   10                  15
```

<210> SEQ ID NO 9
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 9

```
Glu Lys Arg Cys Leu Asn Pro Glu Ser Lys Ala Ile Lys Asn Leu
1               5                   10                  15
```

<210> SEQ ID NO 10
<211> LENGTH: 15
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 10

```
Asn Leu Leu Lys Ala Val Ser Lys Glu Arg Ser Lys Arg Ser Pro
1               5                   10                  15
```

<210> SEQ ID NO 11
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 11

```
Pro Glu Ser Lys Ala Ile Lys Asn Leu Leu Lys Ala Val Ser Lys Glu
1               5                   10                  15

Arg Ser Lys Arg Ser Pro
            20
```

```
<210> SEQ ID NO 12
<211> LENGTH: 16
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 12

Lys Asn Leu Leu Lys Ala Val Ser Lys Glu Arg Ser Lys Arg Ser Pro
1               5                   10                  15


<210> SEQ ID NO 13
<211> LENGTH: 39
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 13

Val Pro Leu Ser Arg Thr Val Arg Cys Thr Cys Ile Ser Ile Gly Gly
1               5                   10                  15

Gly Pro Glu Ser Lys Ala Ile Lys Asn Leu Leu Lys Ala Val Ser Lys
            20                  25                  30

Glu Arg Ser Lys Arg Ser Pro
        35


<210> SEQ ID NO 14
<211> LENGTH: 39
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 14

Pro Glu Ser Lys Ala Ile Lys Asn Leu Leu Lys Ala Val Ser Lys Glu
1               5                   10                  15

Arg Ser Lys Arg Ser Pro Gly Gly Gly Val Pro Leu Ser Arg Thr Val
            20                  25                  30

Arg Cys Thr Cys Ile Ser Ile
        35


<210> SEQ ID NO 15
<211> LENGTH: 37
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 15

Leu Ser Arg Thr Val Arg Cys Thr Cys Ile Ser Ile Gly Gly Gly Pro
1               5                   10                  15

Glu Ser Lys Ala Ile Lys Asn Leu Leu Lys Ala Val Ser Lys Glu Arg
            20                  25                  30

Ser Lys Arg Ser Pro
        35


<210> SEQ ID NO 16
<211> LENGTH: 37
<212> TYPE: PRT
<213> ORGANISM: Artificial Sequence
<220> FEATURE:
```

```
<223> OTHER INFORMATION: Artificially synthesized antibacterial peptide
      or conjugate

<400> SEQUENCE: 16

Pro Glu Ser Lys Ala Ile Lys Asn Leu Leu Lys Ala Val Ser Lys Glu
1               5                   10                  15

Arg Ser Lys Arg Ser Pro Gly Gly Gly Leu Ser Arg Thr Val Arg Cys
            20                  25                  30

Thr Cys Ile Ser Ile
        35


<210> SEQ ID NO 17
<211> LENGTH: 35
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 17

Arg Thr Val Arg Cys Thr Cys Ile Ser Ile Gly Gly Gly Pro Glu Ser
1               5                   10                  15

Lys Ala Ile Lys Asn Leu Leu Lys Ala Val Ser Lys Glu Arg Ser Lys
            20                  25                  30

Arg Ser Pro
        35


<210> SEQ ID NO 18
<211> LENGTH: 35
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 18

Pro Glu Ser Lys Ala Ile Lys Asn Leu Leu Lys Ala Val Ser Lys Glu
1               5                   10                  15

Arg Ser Lys Arg Ser Pro Gly Gly Gly Arg Thr Val Arg Cys Thr Cys
            20                  25                  30

Ile Ser Ile
        35


<210> SEQ ID NO 19
<211> LENGTH: 33
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 19

Val Pro Leu Ser Arg Thr Val Arg Cys Thr Cys Ile Ser Ile Gly Gly
1               5                   10                  15

Gly Lys Asn Leu Leu Lys Ala Val Ser Lys Glu Arg Ser Lys Arg Ser
            20                  25                  30

Pro


<210> SEQ ID NO 20
<211> LENGTH: 31
<212> TYPE: PRT
<213> ORGANISM: Artificial Sequence
<220> FEATURE:
```

<223> OTHER INFORMATION: Artificially synthesized antibacterial peptide
      or conjugate

<400> SEQUENCE: 20

Lys Asn Leu Leu Lys Ala Val Ser Lys Glu Arg Ser Lys Arg Ser Pro
1               5                   10                  15

Gly Gly Gly Val Pro Leu Ser Arg Thr Val Arg Cys Thr Cys Ile
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 21

Leu Ser Arg Thr Val Arg Cys Thr Cys Ile Ser Ile Gly Gly Gly Lys
1               5                   10                  15

Asn Leu Leu Lys Ala Val Ser Lys Glu Arg Ser Lys Arg Ser Pro
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 22

Lys Asn Leu Leu Lys Ala Val Ser Lys Glu Arg Ser Lys Arg Ser Pro
1               5                   10                  15

Gly Gly Gly Leu Ser Arg Thr Val Arg Cys Thr Cys Ile Ser Ile
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 23

Arg Thr Val Arg Cys Thr Cys Ile Ser Ile Gly Gly Gly Lys Asn Leu
1               5                   10                  15

Leu Lys Ala Val Ser Lys Glu Arg Ser Lys Arg Ser Pro
            20                  25

<210> SEQ ID NO 24
<211> LENGTH: 27
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 24

Lys Asn Leu Leu Lys Ala Val Ser Lys Glu Arg Ser Lys Arg Ser Pro
1               5                   10                  15

Gly Gly Gly Arg Thr Val Arg Cys Thr Cys Ile
            20                  25

<210> SEQ ID NO 25
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 25

Ala Thr Val Arg Cys Thr Cys Ile
1 5

<210> SEQ ID NO 26
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 26

Arg Ala Val Arg Cys Thr Cys Ile
1 5

<210> SEQ ID NO 27
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 27

Arg Thr Ala Arg Cys Thr Cys Ile
1 5

<210> SEQ ID NO 28
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 28

Arg Thr Val Ala Cys Thr Cys Ile
1 5

<210> SEQ ID NO 29
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 29

Arg Thr Val Arg Ala Thr Cys Ile
1 5

<210> SEQ ID NO 30
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 30

Arg Thr Val Arg Cys Ala Cys Ile
1 5

<210> SEQ ID NO 31
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 31

Arg Thr Val Arg Cys Thr Ala Ile
1 5

<210> SEQ ID NO 32
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 32

Arg Thr Val Arg Cys Thr Cys Ala
1 5

<210> SEQ ID NO 33
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 33

Ala Pro Leu Ser Arg Thr Val Arg Cys Thr Cys Ile Ser Ile
1 5 10

<210> SEQ ID NO 34
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 34

Val Ala Leu Ser Arg Thr Val Arg Cys Thr Cys Ile Ser Ile
1 5 10

<210> SEQ ID NO 35
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 35

Val Pro Ala Ser Arg Thr Val Arg Cys Thr Cys Ile Ser Ile
1 5 10

<210> SEQ ID NO 36
<211> LENGTH: 14
<212> TYPE: PRT

<213> ORGANISM: Artificial Sequence
<220> FEATURE:
<223> OTHER INFORMATION: Artificially synthesized antibacterial peptide or conjugate

<400> SEQUENCE: 36

Val Pro Leu Ala Arg Thr Val Arg Cys Thr Cys Ile Ser Ile
1 5 10

<210> SEQ ID NO 37
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 37

Val Pro Leu Ser Ala Thr Val Arg Cys Thr Cys Ile Ser Ile
1 5 10

<210> SEQ ID NO 38
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 38

Val Pro Leu Ser Arg Ala Val Arg Cys Thr Cys Ile Ser Ile
1 5 10

<210> SEQ ID NO 39
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 39

Val Pro Leu Ser Arg Thr Ala Arg Cys Thr Cys Ile Ser Ile
1 5 10

<210> SEQ ID NO 40
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 40

Val Pro Leu Ser Arg Thr Val Ala Cys Thr Cys Ile Ser Ile
1 5 10

<210> SEQ ID NO 41
<211> LENGTH: 14
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 41

Val Pro Leu Ser Arg Thr Val Arg Ala Thr Cys Ile Ser Ile
1 5 10

```
<210> SEQ ID NO 42
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 42

Val Pro Leu Ser Arg Thr Val Arg Cys Ala Cys Ile Ser Ile
1               5                   10


<210> SEQ ID NO 43
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 43

Val Pro Leu Ser Arg Thr Val Arg Cys Thr Ala Ile Ser Ile
1               5                   10


<210> SEQ ID NO 44
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 44

Val Pro Leu Ser Arg Thr Val Arg Cys Thr Cys Ala Ser Ile
1               5                   10


<210> SEQ ID NO 45
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 45

Val Pro Leu Ser Arg Thr Val Arg Cys Thr Cys Ile Ala Ile
1               5                   10


<210> SEQ ID NO 46
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 46

Val Pro Leu Ser Arg Thr Val Arg Cys Thr Cys Ile Ser Ala
1               5                   10


<210> SEQ ID NO 47
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate
```

<400> SEQUENCE: 47

Ala Glu Ser Lys Ala Ile Lys Asn Leu Leu Lys Ala Val Ser Lys Glu
1               5                   10                  15

Arg Ser Lys Arg Ser Pro
            20

<210> SEQ ID NO 48
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 48

Pro Ala Ser Lys Ala Ile Lys Asn Leu Leu Lys Ala Val Ser Lys Glu
1               5                   10                  15

Arg Ser Lys Arg Ser Pro
            20

<210> SEQ ID NO 49
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 49

Pro Glu Ala Lys Ala Ile Lys Asn Leu Leu Lys Ala Val Ser Lys Glu
1               5                   10                  15

Arg Ser Lys Arg Ser Pro
            20

<210> SEQ ID NO 50
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 50

Pro Glu Ser Ala Ala Ile Lys Asn Leu Leu Lys Ala Val Ser Lys Glu
1               5                   10                  15

Arg Ser Lys Arg Ser Pro
            20

<210> SEQ ID NO 51
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 51

Pro Glu Ser Lys Ala Ala Lys Asn Leu Leu Lys Ala Val Ser Lys Glu
1               5                   10                  15

Arg Ser Lys Arg Ser Pro
            20

<210> SEQ ID NO 52

<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 52

Pro Glu Ser Lys Ala Ile Ala Asn Leu Leu Lys Ala Val Ser Lys Glu
1 5 10 15

Arg Ser Lys Arg Ser Pro
20

<210> SEQ ID NO 53
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 53

Pro Glu Ser Lys Ala Ile Lys Ala Leu Leu Lys Ala Val Ser Lys Glu
1 5 10 15

Arg Ser Lys Arg Ser Pro
20

<210> SEQ ID NO 54
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 54

Pro Glu Ser Lys Ala Ile Lys Asn Ala Leu Lys Ala Val Ser Lys Glu
1 5 10 15

Arg Ser Lys Arg Ser Pro
20

<210> SEQ ID NO 55
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 55

Pro Glu Ser Lys Ala Ile Lys Asn Leu Ala Lys Ala Val Ser Lys Glu
1 5 10 15

Arg Ser Lys Arg Ser Pro
20

<210> SEQ ID NO 56
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 56

Pro Glu Ser Lys Ala Ile Lys Asn Leu Leu Ala Ala Val Ser Lys Glu
1 5 10 15

Arg Ser Lys Arg Ser Pro
20

<210> SEQ ID NO 57
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 57

Pro Glu Ser Lys Ala Ile Lys Asn Leu Leu Lys Ala Ala Ser Lys Glu
1 5 10 15

Arg Ser Lys Arg Ser Pro
20

<210> SEQ ID NO 58
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 58

Pro Glu Ser Lys Ala Ile Lys Asn Leu Leu Lys Ala Val Ala Lys Glu
1 5 10 15

Arg Ser Lys Arg Ser Pro
20

<210> SEQ ID NO 59
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 59

Pro Glu Ser Lys Ala Ile Lys Asn Leu Leu Lys Ala Val Ser Ala Glu
1 5 10 15

Arg Ser Lys Arg Ser Pro
20

<210> SEQ ID NO 60
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 60

Pro Glu Ser Lys Ala Ile Lys Asn Leu Leu Lys Ala Val Ser Lys Ala
1 5 10 15

Arg Ser Lys Arg Ser Pro
20

<210> SEQ ID NO 61
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 61

Pro Glu Ser Lys Ala Ile Lys Asn Leu Leu Lys Ala Val Ser Lys Glu
1 5 10 15

Ala Ser Lys Arg Ser Pro
20

<210> SEQ ID NO 62
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 62

Pro Glu Ser Lys Ala Ile Lys Asn Leu Leu Lys Ala Val Ser Lys Glu
1 5 10 15

Arg Ala Lys Arg Ser Pro
20

<210> SEQ ID NO 63
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 63

Pro Glu Ser Lys Ala Ile Lys Asn Leu Leu Lys Ala Val Ser Lys Glu
1 5 10 15

Arg Ser Ala Arg Ser Pro
20

<210> SEQ ID NO 64
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 64

Pro Glu Ser Lys Ala Ile Lys Asn Leu Leu Lys Ala Val Ser Lys Glu
1 5 10 15

Arg Ser Lys Ala Ser Pro
20

<210> SEQ ID NO 65
<211> LENGTH: 22
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 65

Pro Glu Ser Lys Ala Ile Lys Asn Leu Leu Lys Ala Val Ser Lys Glu
1 5 10 15

Arg Ser Lys Arg Ala Pro
20

```
<210> SEQ ID NO 66
<211> LENGTH: 22
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 66

Pro Glu Ser Lys Ala Ile Lys Asn Leu Leu Lys Ala Val Ser Lys Glu
1               5                   10                  15

Arg Ser Lys Arg Ser Ala
            20


<210> SEQ ID NO 67
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 67

Arg Arg Val Arg Cys Thr Cys Ile
1               5


<210> SEQ ID NO 68
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 68

Arg Asn Val Arg Cys Thr Cys Ile
1               5


<210> SEQ ID NO 69
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 69

Arg Asp Val Arg Cys Thr Cys Ile
1               5


<210> SEQ ID NO 70
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 70

Arg Cys Val Arg Cys Thr Cys Ile
1               5


<210> SEQ ID NO 71
<211> LENGTH: 8
<212> TYPE: PRT
<213> ORGANISM: Artificial Sequence
<220> FEATURE:
<223> OTHER INFORMATION: Artificially synthesized antibacterial peptide
```

or conjugate

<400> SEQUENCE: 71

Arg Glu Val Arg Cys Thr Cys Ile
1 5

<210> SEQ ID NO 72
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 72

Arg Gln Val Arg Cys Thr Cys Ile
1 5

<210> SEQ ID NO 73
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 73

Arg Gly Val Arg Cys Thr Cys Ile
1 5

<210> SEQ ID NO 74
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 74

Arg His Val Arg Cys Thr Cys Ile
1 5

<210> SEQ ID NO 75
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 75

Arg Ile Val Arg Cys Thr Cys Ile
1 5

<210> SEQ ID NO 76
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 76

Arg Leu Val Arg Cys Thr Cys Ile
1 5

<210> SEQ ID NO 77

<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 77

Arg Lys Val Arg Cys Thr Cys Ile
1               5

<210> SEQ ID NO 78
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 78

Arg Met Val Arg Cys Thr Cys Ile
1               5

<210> SEQ ID NO 79
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 79

Arg Phe Val Arg Cys Thr Cys Ile
1               5

<210> SEQ ID NO 80
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 80

Arg Pro Val Arg Cys Thr Cys Ile
1               5

<210> SEQ ID NO 81
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 81

Arg Ser Val Arg Cys Thr Cys Ile
1               5

<210> SEQ ID NO 82
<211> LENGTH: 8
<212> TYPE: PRT
<213> ORGANISM: Artificial Sequence
<220> FEATURE:
<223> OTHER INFORMATION: Artificially synthesized antibacterial peptide or conjugate

<400> SEQUENCE: 82

```
Arg Trp Val Arg Cys Thr Cys Ile
1               5


<210> SEQ ID NO 83
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 83

Arg Tyr Val Arg Cys Thr Cys Ile
1               5


<210> SEQ ID NO 84
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 84

Arg Val Val Arg Cys Thr Cys Ile
1               5


<210> SEQ ID NO 85
<211> LENGTH: 8
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 85

Arg Thr Val Arg Cys Pro Cys Ile
1               5


<210> SEQ ID NO 86
<211> LENGTH: 14
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 86

Cys Ser Val Pro Thr Ile Thr Cys Arg Val Arg Leu Ile Ser
1               5                   10


<210> SEQ ID NO 87
<211> LENGTH: 24
<212> TYPE: PRT
<213> ORGANISM: Artificial Sequence
<220> FEATURE:
<223> OTHER INFORMATION: Artificially synthesized antibacterial peptide
      or conjugate

<400> SEQUENCE: 87

Arg Thr Val Arg Cys Thr Cys Ile Arg Thr Val Arg Cys Thr Cys Ile
1               5                   10                  15

Arg Thr Val Arg Cys Thr Cys Ile
            20


<210> SEQ ID NO 88
<211> LENGTH: 30
```

<212> TYPE: PRT
<213> ORGANISM: Artificial Sequence
<220> FEATURE:
<223> OTHER INFORMATION: Artificially synthesized antibacterial peptide or conjugate

<400> SEQUENCE: 88

Arg Thr Val Arg Cys Thr Cys Ile Gly Gly Gly Arg Thr Val Arg Cys
1 5 10 15

Thr Cys Ile Gly Gly Gly Arg Thr Val Arg Cys Thr Cys Ile
20 25 30

<210> SEQ ID NO 89
<211> LENGTH: 22
<212> TYPE: PRT
<213> ORGANISM: Artificial Sequence
<220> FEATURE:
<223> OTHER INFORMATION: Artificially synthesized antibacterial peptide or conjugate
<220> FEATURE:
<221> NAME/KEY: misc_feature
<222> LOCATION: (8)..(8)
<223> OTHER INFORMATION: Xaa is 2-(4-pentenyl)alanine
<220> FEATURE:
<221> NAME/KEY: misc_feature
<222> LOCATION: (12)..(12)
<223> OTHER INFORMATION: Xaa is 2-(4-pentenyl)alanine

<400> SEQUENCE: 89

Pro Glu Ser Lys Ala Ile Lys Xaa Leu Leu Lys Xaa Val Ser Lys Glu
1 5 10 15

Arg Ser Lys Arg Ser Pro
20

<210> SEQ ID NO 90
<211> LENGTH: 22
<212> TYPE: PRT
<213> ORGANISM: Artificial Sequence
<220> FEATURE:
<223> OTHER INFORMATION: Artificially synthesized antibacterial peptide or conjugate
<220> FEATURE:
<221> NAME/KEY: misc_feature
<222> LOCATION: (5)..(5)
<223> OTHER INFORMATION: Xaa is 2-(4-pentenyl)alanine
<220> FEATURE:
<221> NAME/KEY: misc_feature
<222> LOCATION: (12)..(12)
<223> OTHER INFORMATION: Xaa is 2-(4-pentenyl)alanine

<400> SEQUENCE: 90

Pro Glu Ser Lys Xaa Ile Lys Asn Leu Leu Lys Xaa Val Ser Lys Glu
1 5 10 15

Arg Ser Lys Arg Ser Pro
20

<210> SEQ ID NO 91
<211> LENGTH: 22
<212> TYPE: PRT
<213> ORGANISM: Artificial Sequence
<220> FEATURE:
<223> OTHER INFORMATION: Artificially synthesized retro peptide

<400> SEQUENCE: 91

Pro Ser Arg Lys Ser Arg Glu Lys Ser Val Ala Lys Leu Leu Asn Lys
1 5 10 15

Ile Ala Lys Ser Glu Pro
20

```
<210> SEQ ID NO 92
<211> LENGTH: 24
<212> TYPE: PRT
<213> ORGANISM: Artificial Sequence
<220> FEATURE:
<223> OTHER INFORMATION: Artificially synthesized peptide conjugate

<400> SEQUENCE: 92

Arg Thr Val Arg Cys Thr Cys Ile Arg Thr Val Arg Cys Thr Cys Ile
1               5                   10                  15

Arg Thr Val Arg Cys Thr Cys Ile
            20


<210> SEQ ID NO 93
<211> LENGTH: 30
<212> TYPE: PRT
<213> ORGANISM: Artificial Sequence
<220> FEATURE:
<223> OTHER INFORMATION: Artificially synthesized peptide conjugate with
      linkers

<400> SEQUENCE: 93

Arg Thr Val Arg Cys Thr Cys Ile Gly Gly Gly Arg Thr Val Arg Cys
1               5                   10                  15

Thr Cys Ile Gly Gly Gly Arg Thr Val Arg Cys Thr Cys Ile
            20                  25                  30


<210> SEQ ID NO 94
<211> LENGTH: 30
<212> TYPE: PRT
<213> ORGANISM: Artificial Sequence
<220> FEATURE:
<223> OTHER INFORMATION: Artificially synthesized peptide conjugate

<400> SEQUENCE: 94

Arg Thr Val Arg Cys Thr Cys Ile Pro Glu Ser Lys Ala Ile Lys Asn
1               5                   10                  15

Leu Leu Lys Ala Val Ser Lys Glu Arg Ser Lys Arg Ser Pro
            20                  25                  30
```